(12) United States Patent
Ko et al.

(10) Patent No.: US 11,229,481 B2
(45) Date of Patent: Jan. 25, 2022

(54) TREATMENT APPARATUS AND METHOD OF CONTROLLING SAME

(71) Applicant: LUTRONIC CORPORATION, Goyang (KR)

(72) Inventors: Kwang Chon Ko, Paju (KR); Richard Howard Cohen, San Rafael, CA (US)

(73) Assignee: LUTRONIC CORPORATION, Goyang (KR)

(*) Notice: Subject to any disclaimer, the term of this patent is extended or adjusted under 35 U.S.C. 154(b) by 790 days.

(21) Appl. No.: 16/071,413

(22) PCT Filed: Jan. 9, 2018

(86) PCT No.: PCT/KR2018/000418
§ 371 (c)(1),
(2) Date: Jul. 19, 2018

(87) PCT Pub. No.: WO2018/131870
PCT Pub. Date: Jul. 19, 2018

(65) Prior Publication Data
US 2021/0169561 A1  Jun. 10, 2021

(30) Foreign Application Priority Data
Jan. 13, 2017  (KR) .................. 10-2017-0006030

(51) Int. Cl.
*A61B 18/14* (2006.01)
*A61B 18/00* (2006.01)

(52) U.S. Cl.
CPC .. *A61B 18/1477* (2013.01); *A61B 2018/0091* (2013.01); *A61B 2018/00773* (2013.01); *A61B 2018/143* (2013.01)

(58) Field of Classification Search
USPC .......................................... 606/41
See application file for complete search history.

(56) References Cited

U.S. PATENT DOCUMENTS

| 2011/0282188 A1 | 11/2011 | Burnside et al. |
| 2012/0190981 A1* | 7/2012 | Harris .............. A61B 5/150389 |
| | | 600/439 |

(Continued)

FOREIGN PATENT DOCUMENTS

| JP | 2016-104192 A | 6/2016 |
| KR | 10-2011-0000790 A | 1/2011 |

(Continued)

OTHER PUBLICATIONS

International Search Report for PCT/KR2018/000418 filed on Jan. 9, 2018.

*Primary Examiner* — Nicole F Lavert
*Assistant Examiner* — Nicole F Johnson

(57) ABSTRACT

The present invention relates to a treatment apparatus and a method of controlling the same, and provides a treatment apparatus including an insertion unit formed in such a way as to be inserted into a tissue through a tissue surface, a bending sensing unit sensing bending of the insertion unit occurring during insertion, and a controller controlling the insertion operation of the insertion unit based on information sensed by the bending sensing unit, and a method of controlling the same. In accordance with the present invention, there is an advantage in that a treatment effect can be improved because treatment can be performed in the state in which the insertion unit has been inserted into an accurate target location.

25 Claims, 26 Drawing Sheets

(56) References Cited

U.S. PATENT DOCUMENTS

| | | |
|---|---|---|
| 2014/0194789 A1 | 7/2014 | Ko |
| 2014/0303494 A1* | 10/2014 | Janicki ................ A61B 5/0059 |
| | | 600/424 |
| 2014/0350536 A1* | 11/2014 | Allison ................ A61B 18/02 |
| | | 606/21 |
| 2017/0202611 A1 | 7/2017 | Shin et al. |

FOREIGN PATENT DOCUMENTS

| | | |
|---|---|---|
| KR | 10-1300123 B1 | 8/2013 |
| KR | 10-2013-0106019 A | 9/2013 |
| KR | 10-1549786 B1 | 9/2015 |
| KR | 10-2016-0099332 A | 8/2016 |

* cited by examiner

TREATMENT APPARATUS AND METHOD OF CONTROLLING SAME

This application is a U.S. National Stage of PCT/KR2018/000418, filed Jan. 9, 2018, which claims the priority benefit of Korean Patent Application No. 10-2017-0006030, filed on Jan. 13, 2017 in the Korean Intellectual Property Office, the disclosures of which are incorporated herein by reference.

TECHNICAL FIELD

The present invention relates to a treatment apparatus and a method of controlling the same and, more particularly, to a treatment apparatus inserted into a tissue of the human body to perform treatment using an invasive method and a method of controlling the same.

BACKGROUND ART

A method of treating a tissue may be divided into a method of treating a tissue outside the tissue and an invasive treatment method of treating a tissue by inserting some of or the entire treatment apparatus into the tissue. The invasive treatment method basically uses a treatment apparatus having a thin-necked insertion unit, such as a needle or a catheter. Treatment is performed after the treatment apparatus is inserted up to a target location within a tissue.

The invasive treatment method includes various treatment behaviors, such as delivering a treating substance to the inside of a tissue, performing surgical treatment through a mechanical operation in the state in which a specific tissue within a tissue is adjacent, or delivering energy to a target location within a tissue. The treatment method has been disclosed in Korean Patent Application Publication No. 10-2011-0000790, and is applied in various methods.

In general, in the invasive treatment method, in a process of inserting an insertion unit into a tissue, displacement may occur as a tissue surface is pressurized. Furthermore, as the diameter of the insertion unit is reduced for minimum invasion, the bending of the insertion unit may occur in the insertion process. Accordingly, the insertion unit is not inserted up to a desired target location. In this case, treatment sensitive to a depth in which the treatment is performed, such as skin treatment, may have a problem in that a treatment effect is low or another tissue is damaged.

DISCLOSURE

Technical Problem

An object of the present invention is to provide a treatment apparatus capable of inserting an insertion unit into an accurate target location although the bending of the insertion unit or displacement of a tissue surface occurs in a process of inserting the insertion unit into a tissue, and a method of controlling the same.

Technical Solution

In order to accomplish the object, the present invention provides a treatment apparatus including an insertion unit formed in such a way as to be inserted into a tissue through a tissue surface, a bending sensing unit sensing bending of the insertion unit occurring during insertion, and a controller controlling the insertion operation of the insertion unit based on information sensed by the bending sensing unit.

When the bending of the insertion unit is sensed by the bending sensing unit, the controller may control the insertion operation of the insertion unit so that the end of the insertion unit reaches a target location in the state in which the bending of the insertion unit has been restored.

Specifically, when the bending of the insertion unit is sensed by the bending sensing unit, the controller may perform control to advance the insertion unit up to a restoration depth at which the bending is restored, wait for a restoration time for which the bending of the insertion unit is restored, and then retract the end of the insertion unit so that the end of the insertion unit reaches the target location. In this case, the restoration depth may be a layer where a layer having a lower insertion resistance characteristic than a surface layer of the tissue is positioned. The restoration time may be between 0.05 second and 1 second.

The restoration time may be the time until the bending of the insertion unit has been restored by the bending sensing unit or the restoration time may be differently set depending on the degree of bending sensed by the bending sensing unit.

The bending sensing unit may be configured to sense whether the bending of the insertion unit occurs based on whether a support plate in which the insertion unit is positioned is inclined. Or, the bending sensing unit may include a motion sensor positioned at a location close to the end of the handpiece and sensing whether the insertion unit has been bent.

Moreover, the treatment apparatus may further include a displacement sensing unit measuring displacement of the tissue surface occurring due to the insertion of the insertion unit. The controller may control the insertion operation of the insertion unit by taking into consideration displacement sensed by the displacement sensing unit. In this case, the controller may additionally insert the insertion unit in accordance with displacement occurring in the tissue surface.

The insertion unit may include a plurality of micro needles. The micro needle may have a diameter of 10 to 1000 μm. Furthermore, the insertion unit may include an energy transfer member transferring energy to the target location in the state in which the insertion unit has been inserted into the tissue.

Moreover, when the bending is sensed to be not restored through the insertion operation, the controller may control to transfer energy having lower output than preset energy to the target location or to not transfer energy to the target location.

Meanwhile, the present invention may provide a treatment apparatus, including a handpiece, an insertion unit formed in such a way as to pop in and out to and from one side of the handpiece and inserted into a tissue to transfer energy to a target location, a bending sensing unit sensing bending of the insertion unit occurring during insertion of the insertion unit, and a controller controlling an insertion operation of the insertion unit based on information sensed by the bending sensing unit.

Furthermore, the present invention may provide a method of controlling a treatment apparatus, including the steps of positioning an insertion unit on a tissue surface, inserting the insertion unit into the tissue by advancing the insertion unit, sensing bending of the insertion unit occurring during the insertion of the insertion unit, and controlling an insertion operation of the insertion unit based on the sensed bending information.

In this case, the step of controlling the insertion operation may include advancing the insertion unit up to a restoration depth at which the bending is restored and then retracting the insertion unit to a target location when the bending of the insertion unit is sensed through a bending sensing unit.

Moreover, the step of controlling the insertion operation may include the step of waiting for a restoration time for which the bending of the insertion unit is stored in the state in which the insertion unit has been advanced up to the restoration depth.

Furthermore, the step of sensing the bending may include sensing the bending by measuring a gradient of the support plate in which the insertion unit is positioned or sensing whether the insertion unit has been bent using a motion sensor positioned at a location close to the end of the handpiece.

Advantageous Effects

In accordance with the present invention, there is an advantage in that a treatment effect can be improved because treatment can be performed in the state in which the insertion unit has been inserted up to an accurate target location. Furthermore, a problem, such as damage to a neighboring tissue occurring because treatment is performed in the state in which the insertion unit has not been sufficiently inserted up to a target location, can be prevented.

MODE FOR INVENTION

Hereinafter, a treatment apparatus according to embodiments of the present invention are described in detail with reference to the drawings. In the following description, the location relations between elements are described in principle based on the drawings. Furthermore, the drawings may be enlarged and shown in order to simplify the structure of the invention for convenience of description or if necessary. Accordingly, the present invention is not limited thereto, and various devices may be added, changed or omitted.

Hereinafter, a "treatment apparatus" includes all apparatuses for treating mammals including people. The treatment apparatus may include may include various treatment apparatuses used to improve a lesion or the state of a tissue. For example, the treatment apparatus includes an apparatus transferring treating substances, such as medicines, anesthetic, and stem cells, an operation apparatus for surgically treating a specific tissue, and various treatment apparatuses transferring RF energy.

Hereinafter, a "tissue" means a set of cells forming various body organs of an animal including people, and includes various tissues forming various organs within the body, including a skin tissue.

Hereinafter, an "insertion unit" means an element that belongs to a treatment apparatus and that is inserted into a tissue. The insertion unit has a lengthy structure having a sharp and thin end, such as a needle, micro needle or a catheter, and includes various structures inserted into a tissue through a surface of the tissue.

Hereinafter, a treatment apparatus according to an embodiment of the present invention is described with reference to FIGS. 1 to 17.

Figure 1:
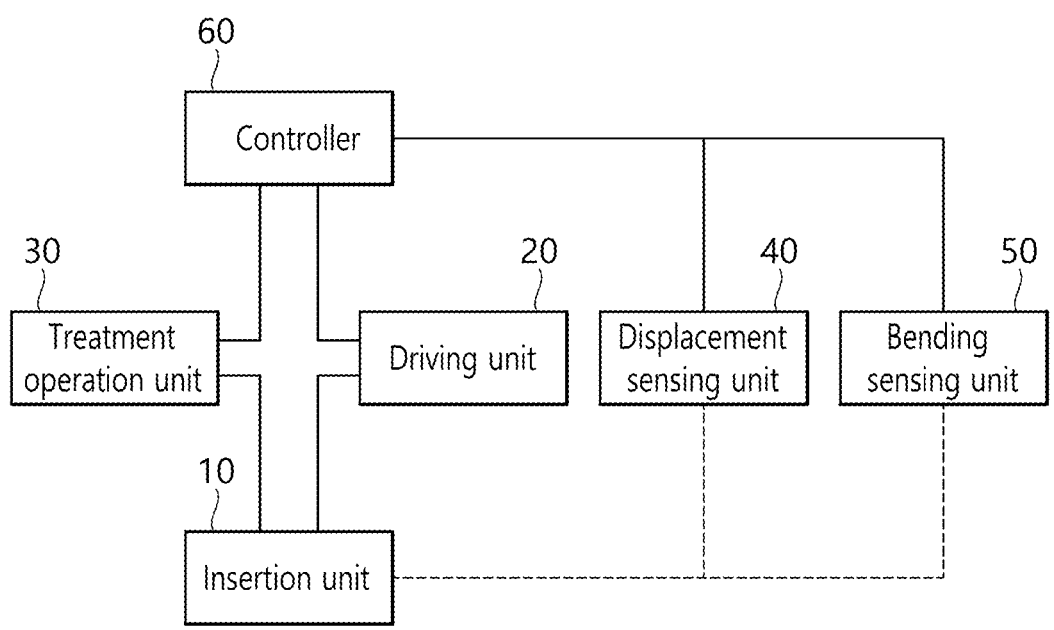
FIG. 1 is a block diagram showing the configuration of a treatment apparatus according to a first embodiment of the present invention.

FIG. 1 is a block diagram showing the configuration of a treatment apparatus according to a first embodiment of the present invention. As shown in FIG. 1, the treatment apparatus according to the present invention includes an insertion unit 10 formed in such a way as to be inserted into a tissue, a driving unit 20 moving the insertion unit, a treatment operation unit 30 for performing treatment on a tissue through the insertion unit, a displacement sensing unit 40 for sensing displacement of a tissue surface, and a controller 60 controlling the operations of various elements, including a state sensing unit for sensing the state of the insertion unit occurring during treatment, the driving unit, and the treatment operation unit.

The insertion unit 10 is an element inserted up to a tissue through a tissue surface as described above. The insertion unit 10 has a lengthy structure having a sharp end and a small diameter so that it can be easily inserted into a tissue. In the present embodiment, the insertion unit 10 includes a plurality of needles, but may have various structures, such as a singular needle structure or catheter. For example, the insertion unit 10 may include a plurality of micro needles. The micro needle may be a needle having a diameter of a range of several to several thousands of μm, and may preferably use a needle having a diameter of 10 to 1000 μm.

The insertion unit 10 further includes an element necessary for the execution of treatment depending on a treatment method of the treatment apparatus. For example, in the case of a treatment apparatus that performs treatment using a method of transferring a treatment substance, the insertion unit may include a channel for injecting a treatment substance therein. Alternatively, in the case of a treatment apparatus that performs treatment using a method of transferring RF energy to the inside of a tissue, the insertion unit may include an electrode for transferring RF energy. The insertion unit 10 is positioned in a handpiece, and may be configured to be advanced and retracted to and from the end of the handpiece and inserted into a tissue.

The driving unit 20 is an element that linearly moves the insertion unit 10 so that the insertion unit advances and retracts. The insertion unit 10 performs an operation of being inserted into a tissue or drawn out from a tissue by the driving of the driving unit 20. For example, the driving unit 20 may be configured using an actuator or may be configured using various driving members.

The treatment operation unit 30 is an element operating for the execution of treatment. The location where treatment is actually performed is the end of the insertion unit 10 positioned within a tissue. The treatment operation unit 30 is an element supporting a treatment operation performed at the end of the insertion unit. For example, the treatment operation unit 30 may have a pump or valve for transferring a treatment substance from a treatment substance accommodation unit (not shown) to the end of the insertion unit. For another example, the treatment operation unit may be an RF generator for supplying RF energy to the end of the insertion unit. In addition, the treatment operation unit may have various elements depending on a treatment method of the treatment apparatus.

The controller 60 controls the operations of various elements of the treatment apparatus, including the driving unit 20 and the treatment operation unit 30. The controller 60 may perform treatment by driving the elements based on a user's control or a preset mode. The controller may further include a separate database or processor. Accordingly, when a variety of types of information necessary for control is transmitted to the controller, the controller may derive a proper control signal using previously stored data or a calculation method based on such information.

Meanwhile, the sensing units 40 and 50 are elements for sensing major parameters while the treatment apparatus operates. The sensing unit may include various sensors for measuring necessary parameters. The sensing unit of the present embodiment may include the displacement sensing unit and/or the state sensing unit, for example.

The displacement sensing unit 40 measures a gap occurring between the end of a handpiece and a tissue surface when the insertion unit 10 is inserted into a tissue, more specifically, displacement of a tissue surface occurring when the insertion unit is inserted. The displacement of a tissue surface occurs due to pressurization or a friction force due to the insertion unit during insertion. The displacement affects the depth of a needle inserted into a tissue. Accordingly, a value measured by the displacement sensing unit 40 is transmitted to the controller 60. The controller 60 may control the insertion operation of the insertion unit 10 based on the value.

Hereinafter, displacement occurring when the insertion unit is inserted is described more specifically with reference to FIGS. 2 to 5. FIGS. 2 to 5 are schematic diagrams showing an example of a treatment step by the treatment apparatus of FIG. 1, and show a process of performing treatment by inserting the insertion unit into a target location of a depth D within a tissue.

Figure 2:
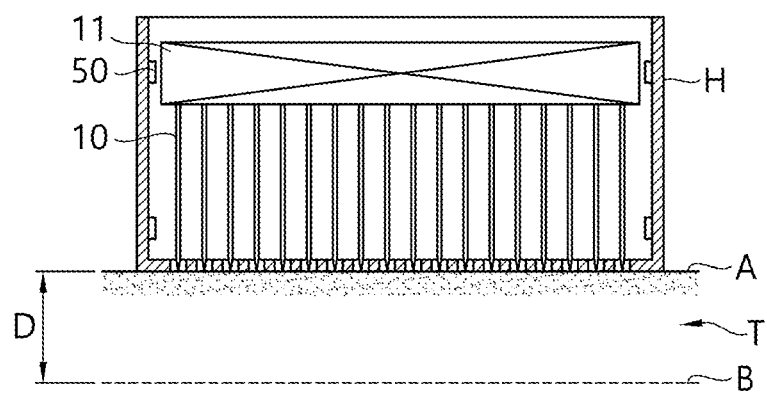
FIGS. 2 to 5 are schematic diagrams showing an example of a treatment step by the treatment apparatus of FIG. 1.

FIG. 2 shows the state in which a handpiece H has been positioned on a surface of a tissue T. This step may be the state in which the driving unit has never been driven, and may be the state in which the driving unit has started to operate, but the end of the insertion unit has not come into contact with a tissue surface. As described above, FIG. 2 shows the state in which the insertion unit 10 has not pressurized a surface A of the tissue. Accordingly, separate displacement does not occur in the tissue surface, and separate displacement does not occur at a target location.

Figure 3:
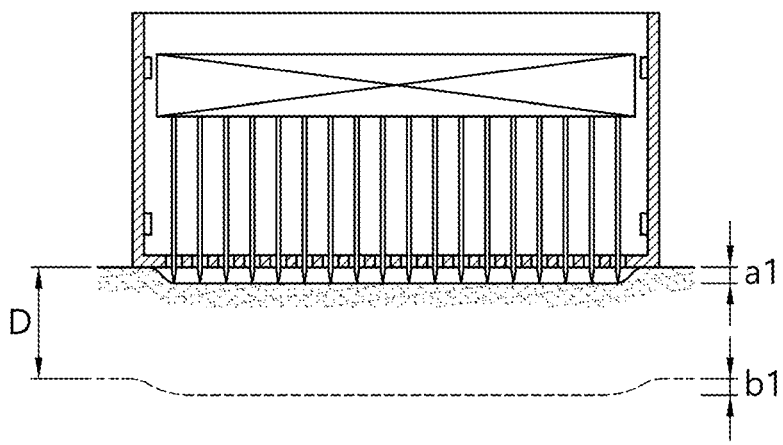

FIG. 3 shows the state in which the driving unit 20 operates and thus the end of the insertion unit 10 has pressurized the surface of the tissue. At the early stage of the insertion operation of the insertion unit 10, the surface of the tissue is pressurized in the state in which it has not been penetrated by the insertion unit. Accordingly, the surface A of the tissue experiences displacement of a1 in the inward direction of the tissue. The tissue has a structure in which cells, etc. have been organized with high density. Accordingly, when displacement occurs on the surface A of the tissue, a target location B also experiences displacement of b1 in the inward direction of the tissue.

Figure 4:
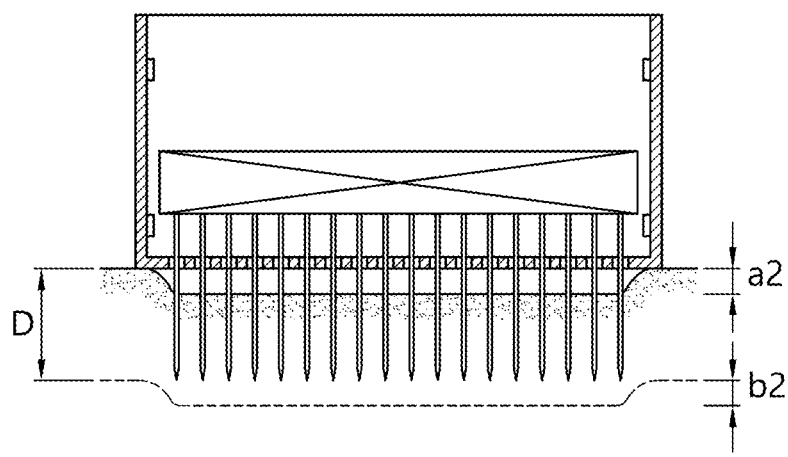

FIG. 4 shows the state in which the insertion unit 10 has been inserted into the tissue by advancing the insertion unit by a first length. In this case, the first length may be a length corresponding to D (depth with respect to a surface before the tissue surface is pressurized by the insertion unit), that is, the depth of the target location before the insertion unit is inserted into the tissue.

As shown in FIG. 4, in this state, the surface of the tissue experiences displacement of a2 in the inward direction of the tissue, and the target location also experiences displacement of b2 in the inward direction of the tissue. The reason for this is that while the insertion unit 10 is inserted, a force acts in the direction in which displacement further occurs by a friction force and the restoration of displacement is limited by the elasticity of the tissue. Accordingly, the tissue can maintain a pressurized state in the state in which the insertion unit has been inserted, and the state in which displacement has occurred in the tissue surface and the target location can also be maintained.

As described above, although the insertion unit 10 is controlled to advance by the first length corresponding to the target location B, the end of the insertion unit does not reach the target location B because the depth of the insertion unit 10 inserted into the tissue is smaller than the first length (in this case, the depth of the insertion unit inserted into the tissue may be D ?? a2). Accordingly, the present embodiment performs control for compensating for this. Specifically, the displacement sensing unit 40 measures displacement of the tissue surface. The controller 60 may additionally control the operation of the insertion unit based on the measured displacement so that the end of the insertion unit 10 reaches the target location.

Figure 5:
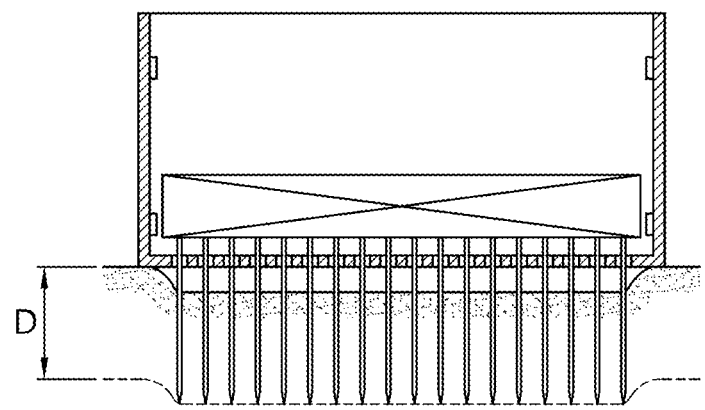

FIG. 5 is the state in which the insertion unit has been additionally inserted by a second length in FIG. 4. In this case, the second length corresponds to a compensation depth by tissue displacement. By additionally inserting the insertion unit 10 by the second length as shown in FIG. 5, the end of the insertion unit can reach the target location, and thus treatment may be performed.

Description is given based on FIG. 1. The displacement sensing unit 40 is an element that measures displacement occurring in a surface of a tissue while the insertion unit is inserted. The displacement sensing unit 40 may be configured using various sensor devices capable of measuring displacement.

For example, the displacement sensing unit 40 may be configured using a photosensor positioned to neighbor a contact surface of the handpiece H coming into contact with the surface of the tissue. The photosensor may radiate light to the surface of the tissue and measure displacement of the surface by receiving light reflected by the surface. For another example, the displacement sensing unit may include a movable member positioned to be movable in response to displacement of the tissue surface and a displacement sensing unit and a sensing member measuring the amount of movement of the movable member. Specifically, the movable member is positioned to be supported by the surface of the tissue in the state in which it can freely move vertically. When the movable member moves by an amount corresponding to displacement occurred when tissue displacement occurs, the sensing member may measure displacement of the tissue surface by measuring the amount of movement of the movable member.

Meanwhile, the controller 60 may determine a value of the second length corresponding to a compensation depth based on displacement of a tissue surface measured by the displacement sensing unit 40. In this case, the value of the second length may be a displacement value of a target location that is expected based on the displacement of the tissue surface. In this case, the characteristics of the tissue are different depending on a treatment portion, race, age, etc. The second length may be determined in various manners by taking into consideration the characteristics of the tissue.

For example, if a tissue corresponding to a treatment location has a low elasticity characteristic or if insertion has already been performed on a tissue in a pressurized state, displacement of a tissue surface and displacement within the tissue have almost a similar size. In this case, the controller 60 may determine a value of the second length to be the same as the displacement of the tissue surface.

Figure 6:
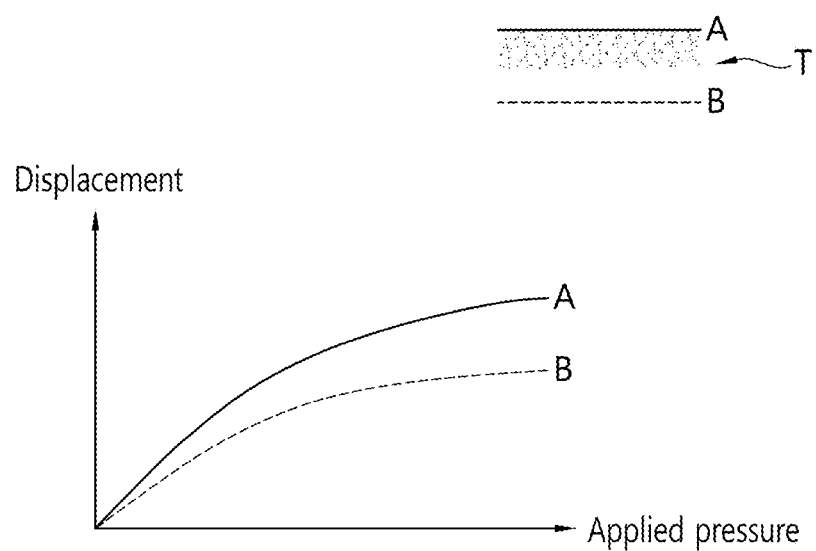
FIG. 6 is a graph showing the displacement characteristics of some tissues according to applied pressure.

In contrast, if a tissue has high elasticity, displacement of a tissue surface and displacement within the tissue may be different. For example, FIG. 6 is a graph showing the displacement characteristics of some tissues according to applied pressure. As shown in FIG. 6, in the state in which pressurization has been applied by the same force, relatively great displacement occurs on a tissue surface, whereas relatively small displacement occurs toward the inside of the tissue. In the case of a tissue having different displacement depending on the depth as described above, the controller 60 may determine a value of the second length through a separate calculation process using a displacement value of a measured surface as a variable or may determine a value of the second length with reference to the displacement value of the tissue surface and an already stored database.

When the value of the second length is determined as described above, the controller 60 compensates for an insufficient insertion depth by controlling the driving unit 20 so that the insertion unit 10 is additionally inserted by the second length. Accordingly, when the end of the insertion unit 10 reaches a target location, the controller 60 performs treatment at the target location by driving the treatment operation unit 30.

Referring back to FIG. 1, the sensing unit according to the present invention may include the state sensing unit in addition to the displacement sensing unit 40. In this case, the state sensing unit is for sensing the state of the insertion unit while treatment is performed. In this case, the state of the insertion unit may be construed as being various meanings, such as bending information of the insertion unit, damage information, and removal information. Furthermore, the controller may perform a control operation by taking into consideration information about the state of the insertion unit sensed by the state sensing unit in addition to the displacement sensing unit.

For example, as shown in FIG. 1, the state sensing unit according to the present invention may include a bending sensing unit 50 for sensing the bending of the insertion unit occurring during treatment. The insertion unit 10 formed of micro needles has a structure having low resistance to bending. Accordingly, bending may occur while the insertion unit is inserted into a tissue through a tissue surface. The bending of the insertion unit 30 occurs when insertion resistance of a tissue is greater than bending resistance of the insertion unit. The insertion resistance characteristic of a tissue may be determined by various factors, such as the structure, component, density, etc. of each tissue layer. Furthermore, the bending of the insertion unit may occur in the state in which the insertion unit has been inserted into a tissue in addition to a process of pressurizing a surface of the tissue. In the case of a micro needle in which bending has occurred, the elastic force of the micro needle acts as a restoring force. If the insertion resistance characteristic of a tissue is greater than the restoring force of the insertion unit, however, the insertion unit maintains the bent state within the tissue. When bending occurs in the insertion unit as described above, although the driving unit drives the insertion unit so that it advances by a given length, the end of the insertion unit does not sufficiently advance by a target length. Accordingly, the bending sensing unit 50 senses whether the bending of the insertion unit occurs during insertion or the degree of bending occurred. The controller 60 may control an insertion operation or treatment contents based on the information sensed by the bending sensing unit so that an error attributable to the occurrence of bending can be compensated for.

Hereinafter, behavior characteristics according to the bending of the insertion unit are described more specifically with reference to FIGS. 7 to 11. FIGS. 7 to 11 are schematic diagrams showing an example of a treatment step by the treatment apparatus of FIG. 1, and show a process of inserting the insertion unit into a target location of a depth D within a tissue and performing treatment.

Figure 7:
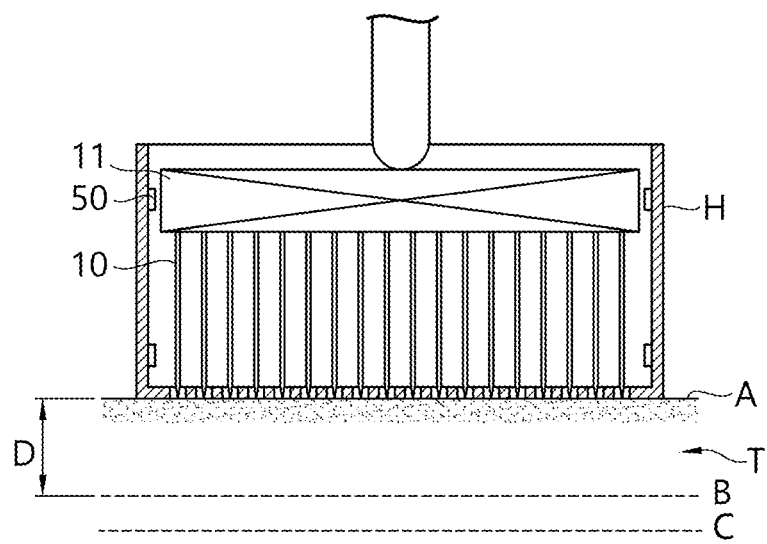
FIGS. 7 to 11 are schematic diagrams showing an example of a treatment step by the treatment apparatus of FIG. 1.
Figure 8:
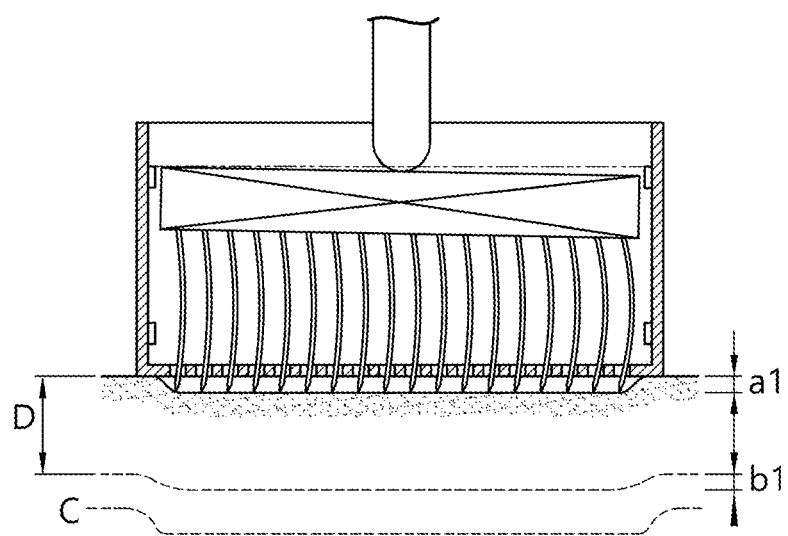

FIG. 7 shows the state in which a handpiece H has been positioned on a surface of a tissue T as in FIG. 2. Furthermore, FIG. 8 shows the state in which the end of the insertion unit 10 has pressurized the surface of the tissue by the driving unit 20. In this case, displacement occurs on the surface A of the tissue as in FIG. 3. Furthermore, bending occurs in the insertion unit because surface tension of the tissue acts as a force resistant to the insertion.

Figure 9:
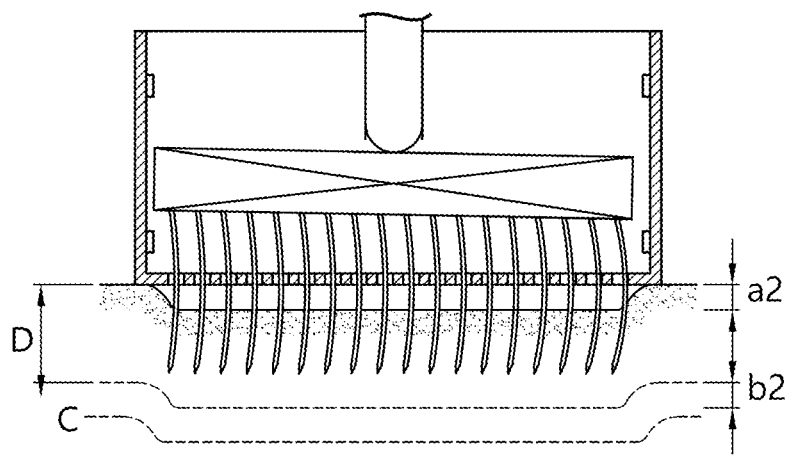

FIG. 9 shows the state in which the driving unit 20 continues to drive the insertion unit 10 by a first length and thus the insertion unit has been inserted into the tissue. The first length is a length corresponding to D, that is, the depth of a target location before the insertion unit 10 pressurizes the tissue. As in FIG. 9, when an insertion resistance characteristic within the tissue is greater than the elastic force of the insertion unit, the insertion unit is inserted into the tissue in the state in which bending has not restored. In this case, although the insertion unit is advanced by the first length with respect to a support plate 11, the insertion unit does not advance by the first length due to the bending with respect to the end of the insertion unit 10. Furthermore, as described above with reference to FIG. 4, the insertion unit may not be inserted into the tissue by the advanced length due to displacement of the tissue attributable to the pressurization of the insertion unit against the tissue.

The end of the insertion unit does not reach the target location B of the tissue due to the bending of the insertion unit and the displacement of the tissue as described above. Furthermore, if the insertion unit is inserted into the tissue in the state in which it has been bent and treatment is performed, there is a danger of damage to a tissue on a retracting path in the process of retracting the insertion unit. Accordingly, the bending sensing unit 50 of the present embodiment senses whether the insertion unit 10 has bent during treatment. The controller 60 controls the insertion operation of the insertion unit 10 based on bending information sensed by the bending sensing unit 50. Furthermore, FIGS. 10 and 8 show an example of insertion control contents for compensating for the occurrence of bending.

Figure 10:
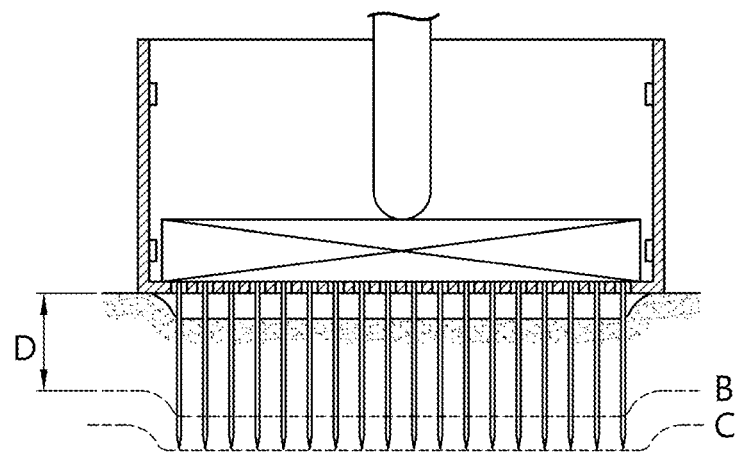

FIG. 10 shows the state in which the end of the insertion unit has been inserted up to a restoration depth C at which the bending of the insertion unit 10 may be restored. In general, the insertion resistance characteristic of a tissue is decreased toward the inside of the tissue. The restoration depth means a depth at which the bending of the insertion unit is restored. A tissue positioned at the restoration depth has an insertion resistance characteristic compared to the surface layer of the tissue. In this case, the restoration depth may be a depth at which a tissue under the dermal layer of a skin tissue is positioned or a depth at which a subcutaneous fat layer is positioned. The insertion unit 10 additionally advances by a third length, and thus the end of the insertion unit reaches the restoration depth. In this case, as described above, the third length may be set by taking into consideration displacement of a tissue occurring in the insertion process of the insertion unit.

As shown in FIG. 10, when the end of the insertion unit 10 reaches the restoration depth C, the bending of the insertion unit 10 is restored by the elasticity of the insertion unit, so the insertion unit can maintain a straight-line state again.

The phenomenon in which the bending of the insertion unit is restored may be achieved while the end of the insertion unit reaches the restoration depth. Alternatively, the insertion unit waits for a specific time in the state in which the end of the insertion unit has reached the restoration depth, and the bending of the insertion unit may be restored during the waiting time. The waiting time (restoration time) may be a previously set time. Alternatively, the waiting time may be differently set based on the degree of bending of the insertion unit sensed by the bending sensing unit 50 in a specific state (e.g., the state in which the insertion unit has advanced up to the first depth). Alternatively, the waiting time may be controlled to be ended when the bending sensing unit senses that the bending of the insertion unit has been restored.

Figure 11:
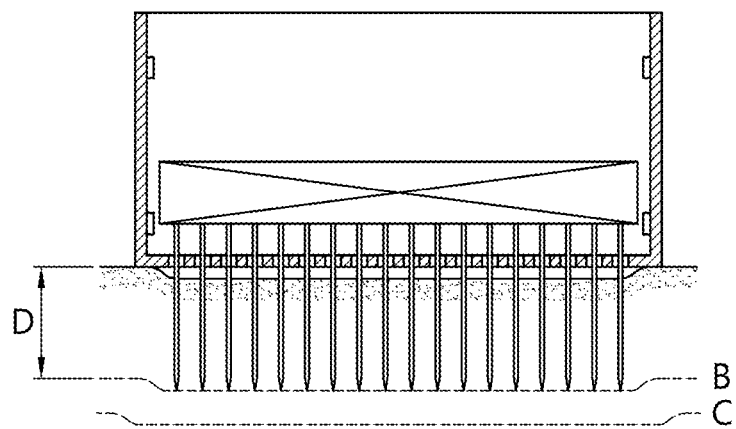

FIG. 11 shows the state in which the insertion unit 10 has been retracted so that the end of the insertion unit is positioned at the target location B in the state in which the bending of the insertion unit has been restored state. While the insertion unit retracts up to the target location B, some of or the entire pressure applied to the tissue may be released or a force having a direction opposite the direction in which a force is applied to the tissue in a previous step may be applied. Accordingly, the length that the insertion unit is retracted in this step may be different depending on the characteristics of the tissue or the depth of the target location and a restoration depth. For example, the lengthy that the insertion unit is retracted in this step may be a difference between the depth C at the restoration location and the depth at the target location B. For another example, the insertion unit may be retracted by the third length additionally advanced in the previous step. Alternatively, the retraction length may be determined with reference to data previously stored in the database. When the end of the insertion unit reaches the target location B through such a step, treatment may be performed at the target location.

Referring back to FIG. 1, in order to perform the aforementioned operation, the bending sensing unit 50 sensing whether the insertion unit has been bent may be configured using various sensor devices.

For example, the bending sensing unit 50 of the present embodiment may determine whether the insertion unit has been bent by sensing the gradient of the support plate 11 where the insertion unit is positioned. In this case, the support plate 11 is a plate-shaped structure in which a plurality of micro needles corresponding to the insertion unit is disposed (refer to FIGS. 2 to 5 and 7 to 11), and may be a PCB for applying current to the plurality of micro needles, for example. As shown in FIGS. 7 to 11, if the support plate is configured in a structure separated from the actuator of the driving unit or connected to be capable of a hinge behavior, the support plate is inclined toward the direction in which the bending of the insertion unit occurs, thus form a slope. Accordingly, the bending generation unit 50 may sense whether bending occurs or the degree of bending by sensing whether the slope of the support plate occurs or the gradient of the support plate.

Specifically, the bending sensing unit 50 may include at least one sensor (not shown) positioned inside the handpiece. The sensors are disposed in the outer circumference of the support plate 11, and may confirm whether the slope of the support plate has occurred by sensing a location at the edge of the support plate at each location.

In addition to the aforementioned element, the bending sensing unit may include a motion sensor positioned at a location close to the end of the handpiece coming into contact with a tissue surface. The motion sensor may include an image sensor for determining whether the insertion unit has been bent. Alternatively, the motion sensor may be configured using a sensor capable of determining a change in the location of a marker (e.g., a magnetic body) formed at the center of the insertion unit.

Figure 12:
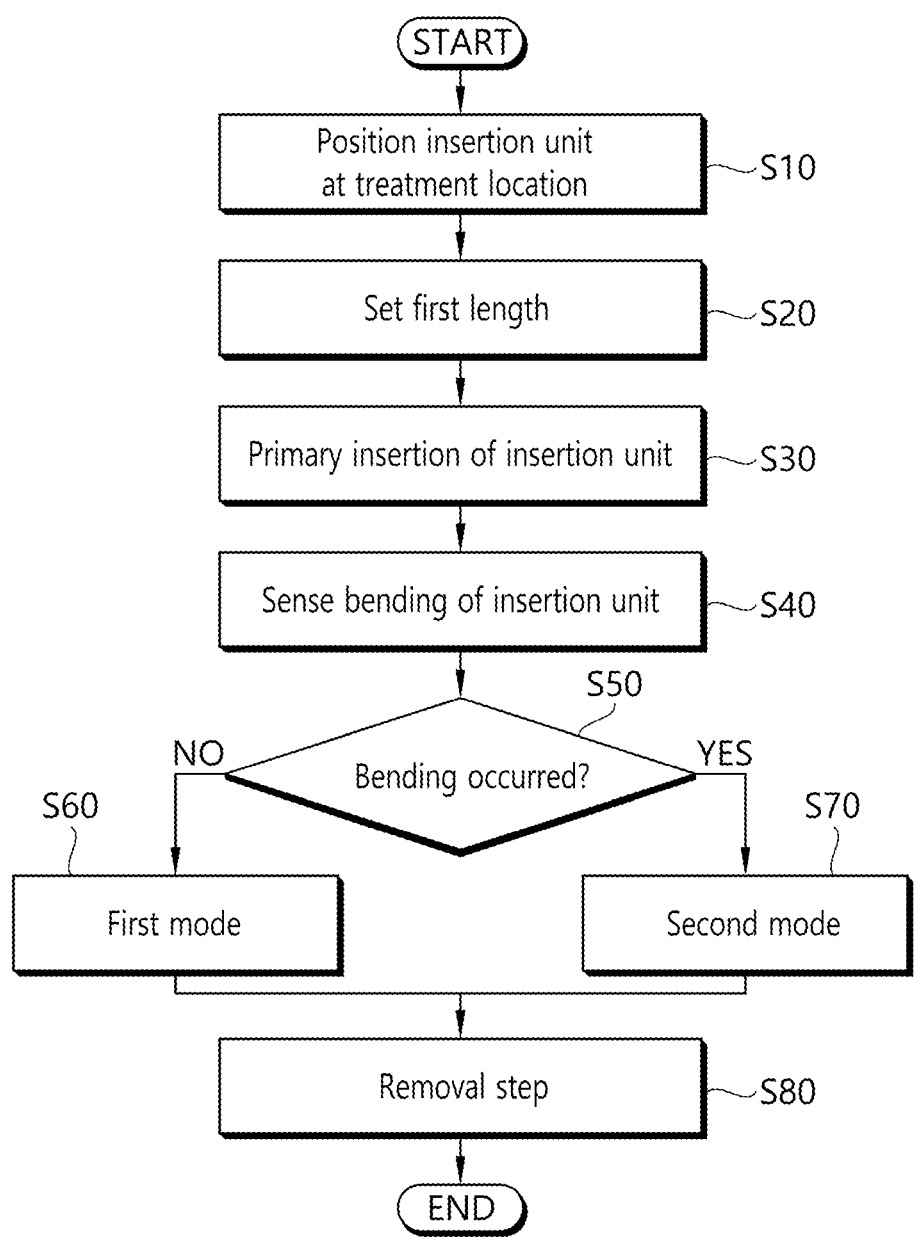
FIG. 12 is a flowchart showing a method of controlling the treatment apparatus of FIG. 1.

FIG. 12 is a flowchart showing a method of controlling the treatment apparatus of FIG. 1. Hereinafter, the method of controlling the treatment apparatus of the present embodiment is described with reference to FIG. 12.

First, the insertion unit 10 of the treatment apparatus is positioned at the treatment location of a tissue (S10). Specifically, one end of the handpiece to and from which the insertion unit 10 is advanced and retracted is positioned to neighbor or come into contact with a surface of the tissue corresponding to the treatment location.

Furthermore, the step of setting a first length is performed (S20). In this case, the first length is set to have a size corresponding to the depth of a target location B within the tissue. For example, the first length may be set as a distance value D from the surface of the tissue that has not been pressurized to the target location. Or, the first length may be set as a distance value from a contact surface of the handpiece coming into contact with the surface of the tissue when treatment is performed to the target location. In this case, if the initial location of the insertion unit has been separated from the surface of the tissue, the first length may be a value of the sum of the distance from the initial location to the tissue surface and the target location from the tissue surface.

Thereafter, the step of primarily inserting the insertion unit is performed (S30). The controller 60 drives the driving unit 20 so that the insertion unit 10 is advanced by the first length and thus inserted into the tissue through the surface of the tissue. In this process, displacement of the tissue occurs as the tissue is pressurized, so the insertion unit 10 may not reach the target location.

When the primary insertion step of the insertion unit 10 is performed, the bending sensing unit 50 performs the step of sensing whether the bending of the insertion unit occurs and/or the degree of bending (S40). For example, the bending sensing unit 50 includes a plurality of sensors included in the handpiece, and may sense bending using a method of measuring a gradient of the support plate 11 in which the insertion unit has been positioned. In this case, in addition to the gradient measurement method, a motion sensor for measuring the behavior of the insertion unit using various methods, such as an image acquisition method and a marker location sensing method as described above, may be used.

The bending information of the insertion unit sensed by the bending sensing unit 50 is transmitted to the controller 60. The controller determines whether the bending of the insertion unit has occurred based on the information transmitted by the bending sensing unit (S50). If, as a result of the determination, it is determined that the degree of the bending of the insertion unit is a reference value or less, the controller determines that bending has not substantially occurred, and controls the insertion operation in a first mode corresponding to a normal mode (S60). Furthermore, if it is determined that the degree of bending is greater than the reference value, the controller determines that bending has substantially occurred, and controls the insertion operation in a second mode for compensating for an error of an insertion depth attributable to the bending (S70). The reference value may be differently set by taking into consideration the length and diameter of a micro needle or the depth of a target location.

Figure 13:
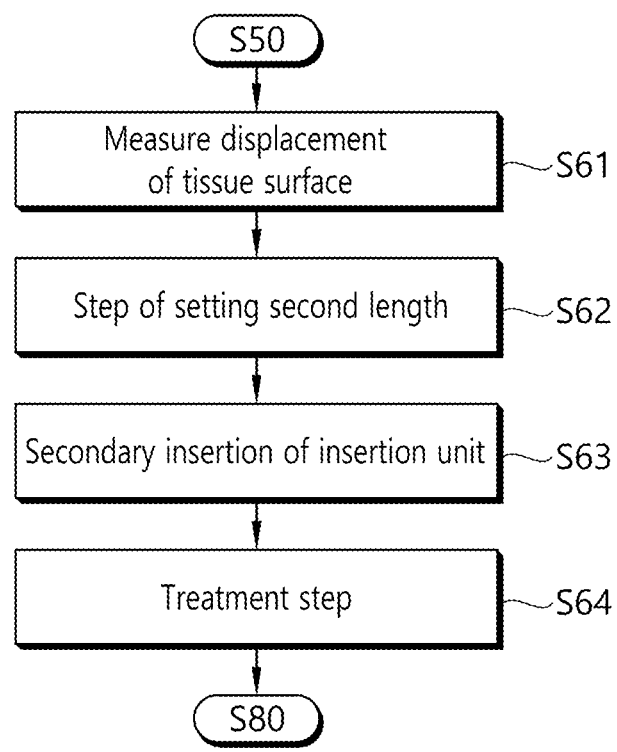
FIG. 13 is a flowchart more specifically showing a first mode in FIG. 12.

FIG. 13 is a flowchart more specifically showing the first mode in FIG. 12. Hereinafter, the first mode is described in detail with reference to FIG. 13.

The displacement sensing unit 40 measures displacement occurred in the tissue surface (S61). FIGS. 12 and 13 show that displacement is sensed after the primary insertion step is terminated, but the present invention is not limited thereto. Displacement may be measured in real time while the primary insertion step is performed. Furthermore, displacement may be measured prior to the bending sensing step or simultaneously with the bending sensing step.

The displacement measured in this step may be displacement in which a tissue surface right before the insertion unit 10 pressurizes the tissue surface is a reference location. In this step, displacement of the tissue surface may be measured in the state in which the insertion unit 10 has completed the primary insertion step. In this case, if it is determined that a difference between values is minute depending on the characteristics of a tissue, for the consecutive execution of subsequent steps, a surface displacement value when the insertion unit penetrates the tissue surface or a surface displacement value while the insertion unit performs the primary insertion step may be measured and used. The displacement sensing unit 40 measures displacement using the aforementioned various sensing methods. The measured displacement value is transmitted to the controller 60.

The controller 60 sets a second length corresponding to a compensation depth based on the measured displacement value (S62). A value of the second length may be determined using various methods as described above. For example, the second length may be set as the same value as a displacement value of the tissue surface sensed by the displacement sensing unit. Alternatively, the value of the second length may be obtained through a separate calculation process using a displacement value of the tissue surface as a variable or may be determined with reference to the displacement value of the tissue surface and a preset database.

When the second length is set, the controller 60 additionally controls the insertion operation of the insertion unit 10 based on the set second length (S63). This step is a secondary insertion step, and includes additionally inserting the insertion unit by the second length by driving the driving unit 20. Accordingly, the end of the insertion unit 10 may reach up to the target location.

When the end of the insertion unit 10 reaches the target location, the controller 60 performs a treatment step by driving the treatment operation unit 30 (S64). This step may be performed in various forms depending on a treatment method of the treatment apparatus. For example, a treatment substance from the treatment operation unit may be transferred and injected into the target location through the end of the insertion unit. Alternatively, the treatment operation unit may generate RF energy and deliver electrical energy to the target location through an electrode at the end of the insertion unit.

When the treatment is terminated through the aforementioned process, the controller 60 terminates the operation of the treatment operation unit 30 and performs the step of retracting the insertion unit 10 by controlling the driving unit 20 (S80). Through this step, the insertion unit 10 inserted into the tissue is drawn out from the tissue surface, so the treatment at the corresponding treatment location may be completed.

Figure 14:
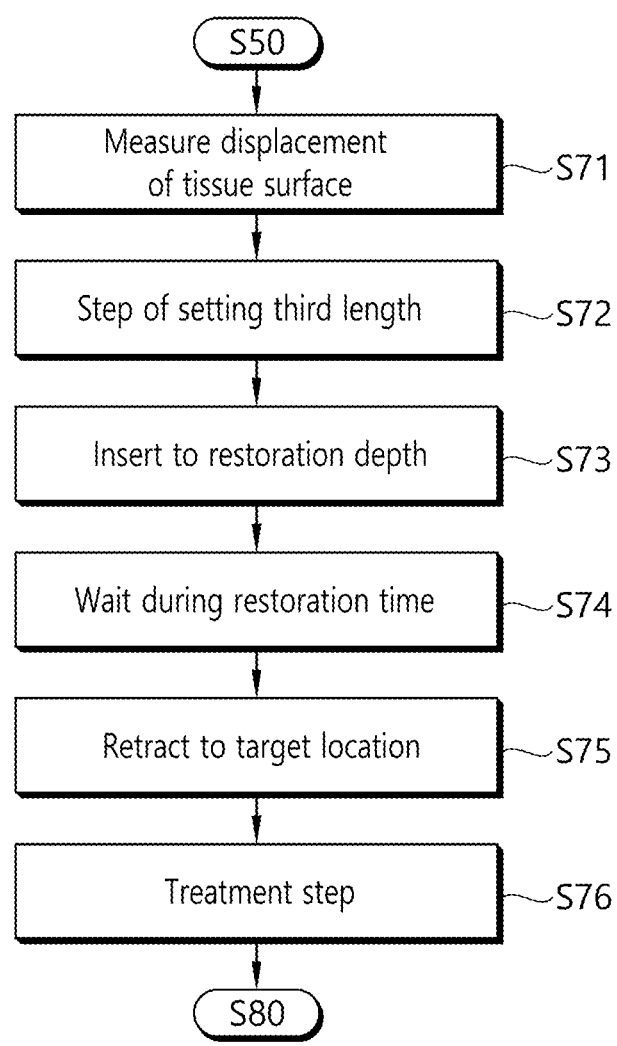
FIG. 14 is a flowchart showing the steps of a second mode in FIG. 12.

Meanwhile, when the occurrence of bending of the insertion unit is sensed in the bending sensing step, the controller controls the insertion operation of the insertion unit in the second mode. FIG. 14 is a flowchart showing the steps of the second mode in FIG. 12. Hereinafter, the first mode is described in detail with reference to FIG. 14.

First, as shown in FIG. 14, the displacement sensing unit 50 measures displacement occurred in the tissue surface (S71). As in S61 of the first mode, in this step, the displacement is measured by the displacement sensing unit, and the measured value is transmitted to the controller. In this case, compared to the first mode, in the second mode, not only pressurization attributable to the driving of the driving unit, but a restoring force attributable to the bending of the insertion unit acts on the tissue surface. Accordingly, slightly great displacement may be sensed compared to the tissue surface displacement occurring in the first mode.

The controller 60 sets a third length, that is, an additional advancing length by which the end of the insertion unit reaches a restoration depth (S72). As described above, the restoration depth is a depth at which ?? of the insertion unit may be restored because the tissue has weak insertion resistance, and may be determined by taking into consideration the structure of the insertion unit and characteristic information of a diseased part. The restoration depth may be determined using a value set by a user or using information stored in the database.

In this step, the controller 60 calculates the third length for reaching the restoration depth by taking into consideration a displacement value sensed by the displacement measurement unit 40. This is similar to the method of calculating the second length in the first mode, and thus a detailed description thereof is omitted.

When the third length is set, the controller 60 additionally inserts the insertion unit by driving the driving unit 20 so that the end of the insertion unit reaches the restoration depth (S73).

Furthermore, the insertion unit waits for a given restoration time in the state in which the end of the insertion unit has been located at the restoration depth (S74). While this step is performed, the insertion unit 10 may be restored in a straight line using its own elastic restoring force generated by bending within the tissue having weak insertion resistance. In this case, as described above, the restoration time may be determined in various manners and may be preferably between 0.05 second and 1 second.

In this case, FIG. 14 shows the waiting step for the restoration time. In the case where a restoration depth and tissue characteristics are taken into consideration, if the bending of the insertion unit is expected to be restored while the step S73 is performed, this step may be omitted without a separate waiting time.

When the bending of the insertion unit is restored through the aforementioned step, the controller 60 performs an operation of retracting the insertion unit 10 up to the target location B by driving the driving unit 20 (S75). In this case, the length that the insertion unit is retracted may be set in various manners as described above. In setting the retracting length, the retracting length may be set by additionally taking into consideration displacement of the tissue occurring upon retraction. Through this step, the end of the insertion unit is located at the target location. At this time, the micro needles corresponding to the insertion unit may maintain a straight line shape.

In this state, as in the first mode, the controller 60 performs a treatment step by driving the treatment operation unit 30. When the treatment step is completed, the controller retracts the insertion unit by controlling the driving unit, thereby terminating the treatment.

An operation of the second mode for compensating for an error attributable to the bending of the insertion unit has been described based on FIG. 14. In addition, the operation contents of the second mode may be configured in various manners. Various modified examples of the second mode are described below with reference to FIGS. 15 to 17.

Figure 15:
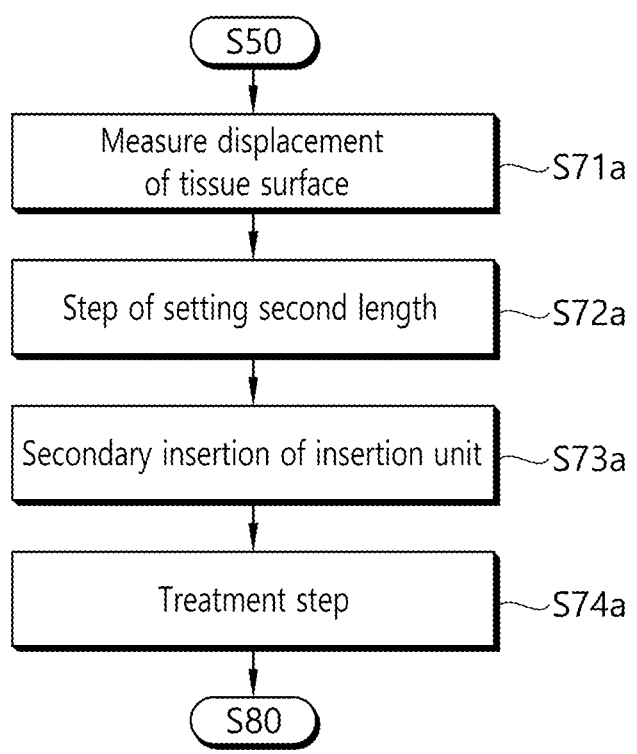
FIG. 15 is a flowchart showing the steps of a modified example of the second mode in FIG. 12.

FIG. 15 is a flowchart showing the steps of a modified example of the second mode in FIG. 12. The second mode shown in FIG. 14 is a method including the step of restoring bending so that treatment can be performed in the state in which the bending of the insertion unit has been restored. In this case, if damage to the tissue rarely occurs although the insertion unit is advanced or retracted in the state in which the insertion unit has been bent, the insertion unit may operate up to the target location so that the insertion unit is inserted in the state in which it has been bent and treatment is performed (refer to the second mode shown in FIG. 15).

Description is given based on FIG. 15. Displacement of the tissue surface is measured through the displacement sensing unit (S71a). Furthermore, the controller set the second length in which the end of the insertion unit may reach the target location (S72a).

In this case, the step S62 of setting the second length in the first mode is performed by taking into consideration displacement information sensed by the displacement sensing unit, whereas the step S72a of setting the second length in FIG. 15 may be performed by taking into consideration both displacement sensed by the displacement sensing unit 40 and the degree of bending sensed by the bending sensing unit 50. When the bending of the insertion unit 10 occurs as described above, the advancing length of the end of the insertion unit 10 becomes shorter than the advancing length of the support plate 11. Accordingly, the controller 60 sets an additionally inserted second length by adding an error attributable to the occurrence of displacement and an error attributable to the occurrence of bending. In this case, the error attributable to the occurrence of bending may be different depending on the degree of bending. The controller may set an error attributable to the occurrence of bending using the degree of bending and information stored in the database.

When the second length is set using such a method, the controller performs a secondary insertion step by driving the driving unit (S73a). Accordingly, the end of the insertion unit reaches the target location, and a treatment step 74a may be subsequently performed.

Figure 16:
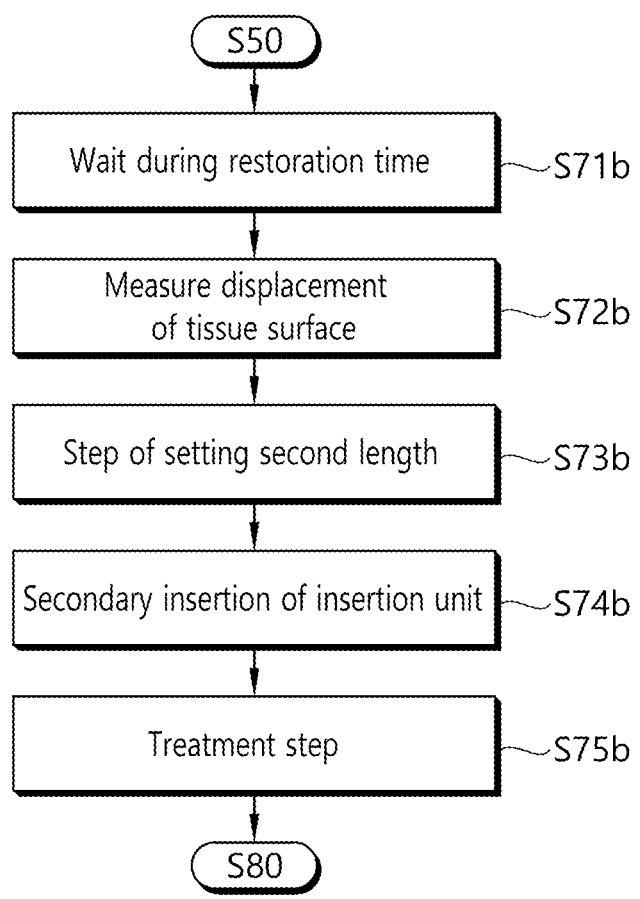
FIG. 16 is a flowchart showing the steps of another modified example of the second mode in FIG. 12.

FIG. 16 is a flowchart showing the steps of another modified example of the second mode in FIG. 12. The second mode shown in FIG. 14 is a method of restoring bending after the insertion unit is additionally advanced up to the restoration depth. In this case, if the location into which the insertion unit has been inserted through the primary insertion step has a low insertion resistance characteristic, the step of separately inserting the insertion unit up to the restoration depth may be omitted.

As shown in FIG. 16, when bending is sensed in the state in which the insertion unit 10 has been inserted into the first depth, a waiting step may be performed without a separate movement so that the bending of the insertion unit is restored (S71b). A restoration time may be between 0.05 second and 1 second. If the target location B is under the dermal layer under the skin or is a tissue having low insertion resistance, such as a subcutaneous fat layer, the waiting step is performed for a given time in the state in which the primary insertion step has been performed. Accordingly, the bending of the insertion unit can be restored by the elastic restoring force of the insertion unit.

Accordingly, when the bending is restored, surface displacement of the tissue may be measured (S72b), a second length may be set (S73b), and a secondary insertion step may be performed by driving the driving unit (S74b). In this modified example, since the bending of the insertion unit has been restored in the step S71b, subsequent steps S72b to S74b may be performed using the same method as the steps S61 to S63 of the first mode. Thereafter, a treatment step S75b is performed at the target location, so the operation of the second mode may be terminated.

Figure 17:
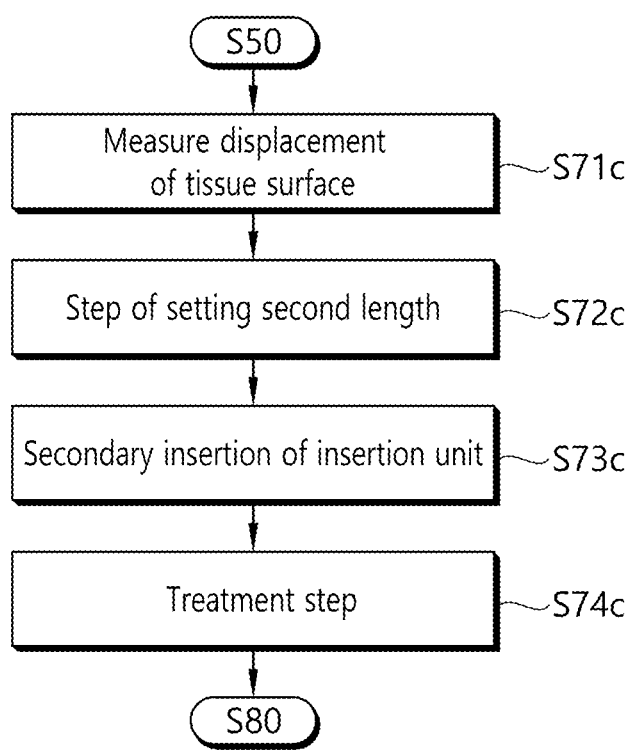
FIG. 17 is a flowchart showing the steps of yet another modified example of the second mode in FIG. 12.

FIG. 17 is a flowchart showing the steps of yet another modified example of the second mode in FIG. 12. The second modes shown in FIGS. 14 to 16 have been focused on a method of reaching, by the end of the insertion unit, a target location in despite of the occurrence of bending. In contrast, the second mode of FIG. 17 may be configured to perform a treatment step differently from the first mode. Specifically, in the second mode of FIG. 17, the steps S71c to S73c of measuring displacement, setting a second length, and performing secondary insertion are performed using the same method as the steps S61 to S63 of the first mode. In this case, since an error attributable to the occurrence of bending is not incorporated, the end of the insertion unit does not reach the target location accurately in the state in which the secondary insertion step has been performed. Accordingly, in performing a treatment step (S74c), the treatment is performed using a parameter different form that in the treatment step S64 of the first mode. For example, if treatment is performed using a method of transferring RF energy through the end of the insertion unit, the RF energy transferred through the end of the insertion unit may be controlled so that it is lower than RF energy transferred in the first mode.

As described above, the second mode controlled by incorporating the occurrence of bending may be performed in various manners as described above. The second mode may be changed in various manners depending on the tissue characteristics of a lesion and a diseased part and performed.

Furthermore, in FIGS. 12 to 17, the execution of the second mode different from that of the first mode corresponding to a normal mode when the occurrence of bending is sensed has been basically described. The second mode may be controlled in such a way as to directly perform a removal step without performing an additional treatment operation when the occurrence of bending is sensed.

The steps of the method of controlling the treatment apparatus according to the present invention have been described above. In FIGS. 12 to 17, the steps have been illustrated as being sequentially performed, but are not limited thereto. The sequence of the steps may be changed and the changed steps may be performed. A plurality of steps may be performed at the same time. For example, the step of setting the first length may be performed before the insertion unit is positioned at the treatment location. Furthermore, the step of measuring displacement may be performed simultaneously with the primary insertion step or may be performed simultaneously with the step of sensing bending. Furthermore, the primary insertion step and the secondary insertion step have been illustrated as being separate steps, but the two steps may be consecutively performed.

In accordance with the aforementioned embodiment, in performing invasive treatment, although a target location is moved due to the insertion of the insertion unit, treatment can be performed at an accurate location by compensating for an insertion depth. Furthermore, although bending occurs in the insertion unit in addition to the occurrence of displacement of a tissue, the step of adjusting an insertion depth or restoring the bending is performed by taking into consideration the occurrence of the bending and the occurrence of displacement of the tissue, thereby being capable of performing treatment at an accurate location and minimizing damage to a tissue.

Hereinafter, other embodiments in which the aforementioned embodiments have been further embodied are described. That is, in the following embodiments, the technical contents of the aforementioned embodiments have been applied to a treatment apparatus for the skin. The elements of the following embodiments corresponding to the elements of the aforementioned embodiments should be construed as being capable of implementing the technical contents of the aforementioned embodiments. In this case, in order to avoid redundant description in describing the present embodiment, a detailed description of contents corresponding to the aforementioned embodiments is omitted.

Figure 18:
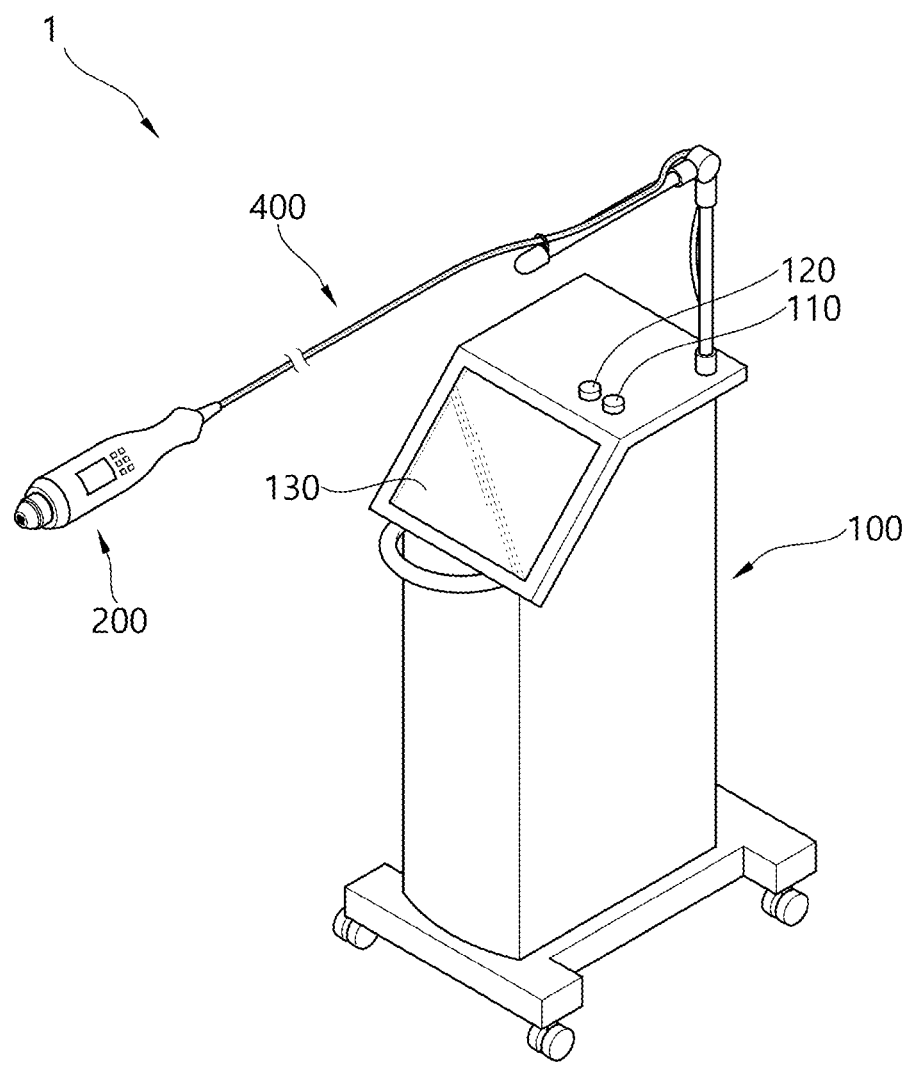
FIG. 18 is a perspective view showing a treatment apparatus according to another embodiment of the present invention.
Figure 19:
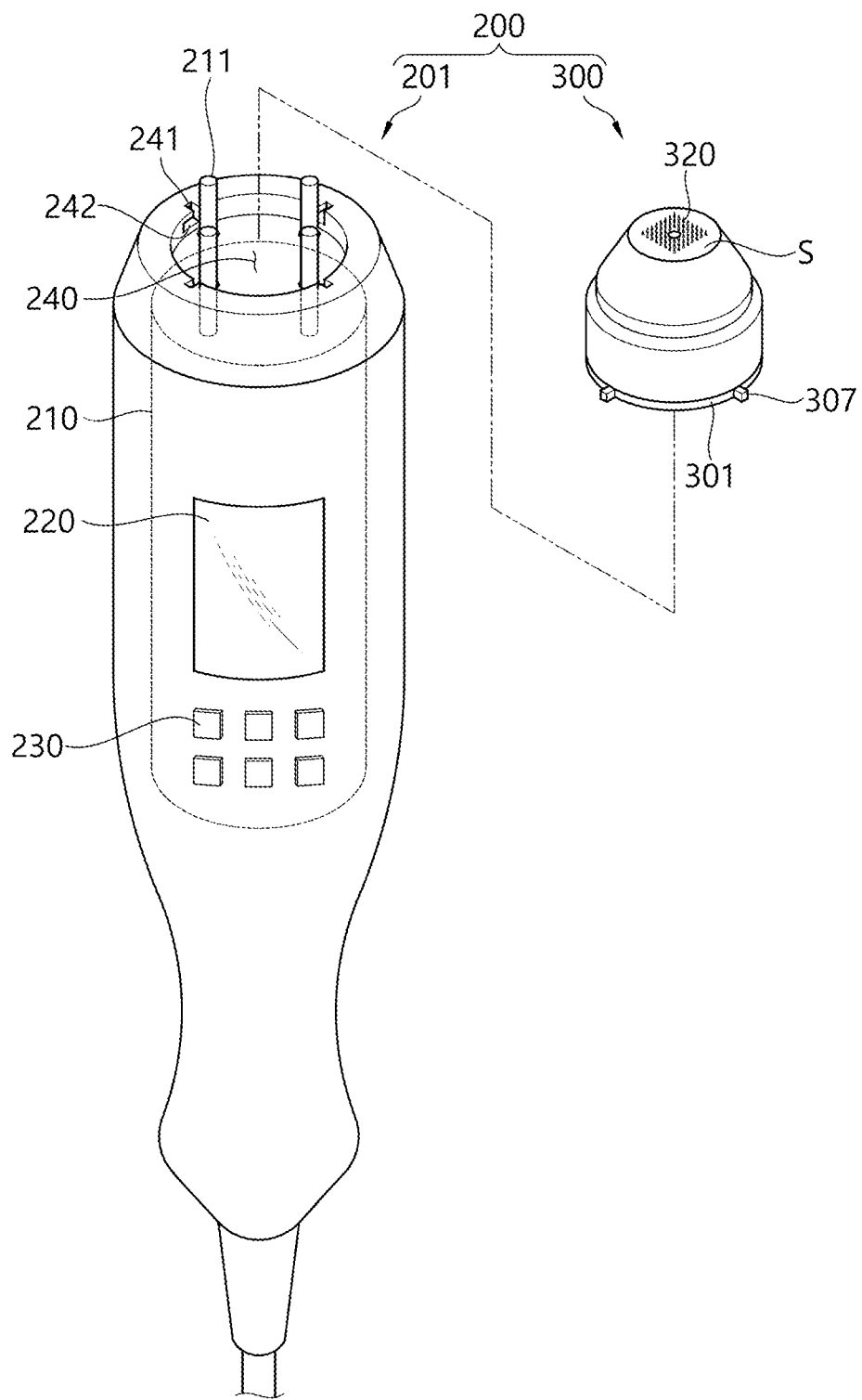
FIG. 19 is a perspective view showing the handpiece of the treatment apparatus of FIG. 18.

FIG. 18 is a perspective view showing a treatment apparatus according to another embodiment of the present invention, and FIG. 19 is a perspective view showing the handpiece of the treatment apparatus of FIG. 18. The treatment apparatus 1 according to the present invention is an apparatus in which the insertion unit is inserted into a skin tissue of the human body and transfers energy to the inside of the skin tissue. In the present embodiment, the insertion unit includes a plurality of micro needles, and may treat a tissue using a fractional treatment method (a method of performing treatment on a location portion area unit separated at the end of each needle by transferring fine energy to the end of the needle) by transferring energy to the inside of a skin tissue through the ends of the micro needles. Referring to FIGS. 18 and 19, the treatment apparatus according to the present invention includes a main body 100, a handpiece 200 that is graphed by a user and through which treatment can be performed, and a connection unit 400 connecting the main body and the handpiece.

An RF generator (not shown) may be provided within the main body 100. The RF generator is an element corresponding to the treatment operation unit (refer to 30 of FIG. 1) of the aforementioned embodiment, and generates RF energy used for treatment. The frequency of the RF energy generated by the RF generator may be controlled depending on the physical constitution, treatment purpose, a treatment portion, etc., of a patient. For example, RF energy used for skin treatment may be adjusted in the range of 0.1 to 0.8 MHz.

A power on/off switch 110, a frequency control lever 120 capable of controlling the frequency of RF energy generated by the RF generator, and a touch screen 130 displaying a variety of types of information including the operating contents of the treatment apparatus, enabling a user to input a command, and displaying treatment information may be positioned on an external surface of the main body 100.

Meanwhile, the handpiece 200 is connected to the main body by the connection unit 400. The connection unit 400 may transfer RF energy generated by the RF generator of the main body to a plurality of needles 320 corresponding to the insertion unit of the aforementioned embodiment, and may transfer power from the main body, which is necessary for various elements on the handpiece side to operate. The connection unit 400 is configured in a cable form, and may use a cable including a plurality of conducting wires whose metal lines are surrounded by insulating coating.

A driving unit 210 is positioned within the handpiece 200. The driving unit 210 is configured to linearly move output terminals 211 provided at the end of the driving unit in the length direction. When the output terminals 211 linearly move, the plurality of needles 320 disposed at the ends of the output terminals may pop in and out to the outside of the contact surface of the handpiece. Accordingly, the plurality of needles 320 may be inserted into a tissue of a patient or drawn out from the tissue by the driving of the driving unit 210. The driving unit 210 may be configured using a linear actuator using a solenoid, a hydraulic/pneumatic cylinder, etc.

A handpiece manipulation unit 230 and a handpiece display unit 220 may be provided on an external surface of the handpiece 200. The handpiece manipulation unit 230 is configured to manipulate the on/off of the handpiece, control the insertion depth of the insertion unit, or control the amount of energy transferred through the insertion unit. The handpiece display unit 220 may display a variety of types of information necessary in a set mode or during treatment with respect to a user. Accordingly, in the state in which the user has graphed the handpiece, the user can easily manipulate treatment contents during treatment through the handpiece manipulation unit 230, and can easily check treatment contents through the handpiece display unit 220.

A tip module 300 is provided at the end of the handpiece. The tip module includes the plurality of needles and may be detachably positioned at the main body 201 of the handpiece. Specifically, a base 301 forms the bottom of the tip module, and outward protruded detachment protrusions 307 are formed at the outer wall of the base. Guide grooves 241 that guides the detachment protrusions and an anti-separation groove 242 for preventing the detachment protrusions 307 guided along the guide grooves 241 from being separated are formed in a recess unit 240 to which the tip module is coupled on the handpiece side. Furthermore, the detachment protrusions 307 of the tip module are disposed at the handpiece in such manner that they are guided along the guide grooves 241 and coupled to the anti-separation groove 242. In this case, an example in which the tip module is detachably positioned at the handpiece as in the present embodiment is illustrative, and the tip module may be integrated with the handpiece.

Figure 20:
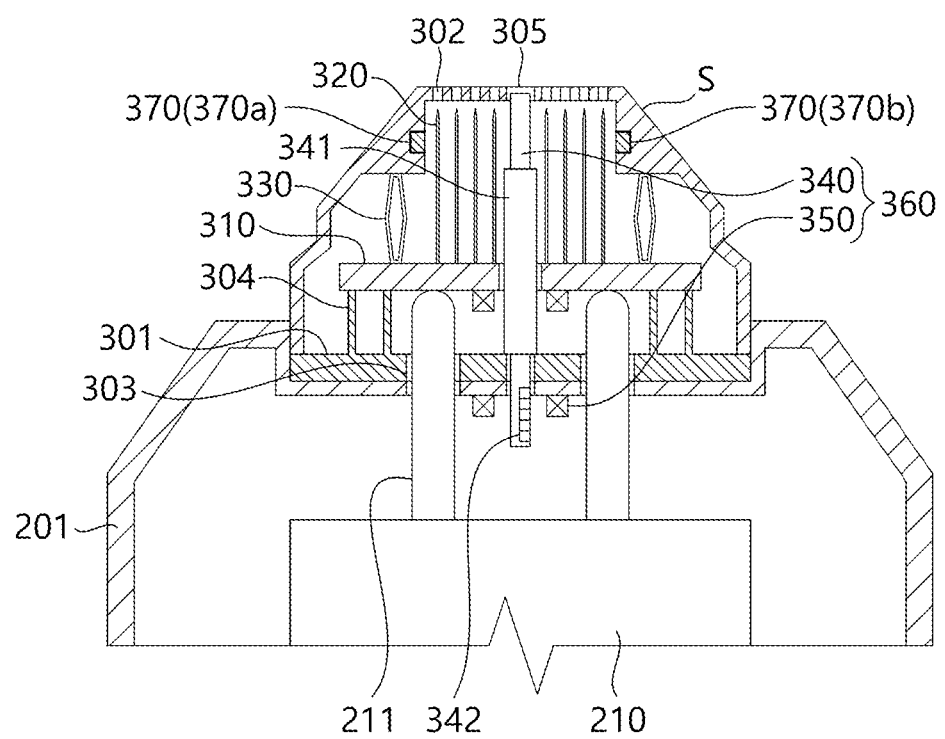
FIG. 20 is a cross-sectional view of the end of the handpiece of FIG. 19.

FIG. 20 is a cross-sectional view of the end of the handpiece of FIG. 19. Referring to FIG. 20, the end of the handpiece 200 is a portion that comes into contact with a skin tissue and where treatment is performed. A support plate 310 in which the plurality of needles 320 is disposed is provided within the tip module. The plurality of needles 320 is fixed and disposed in the support plate 310 in a matrix form. RF energy is transferred to the plurality of needles through a circuit formed in the support plate 310. The front S of the tip module may form a portion that neighbors or comes into contact with the skin of a patient upon treatment. A plurality of through holes 302 through which the plurality of needles pops in and out is formed in the front S.

At least one hole 303 through which the output terminal 211 can pass is provided at the bottom of the tip module. The output terminal 211 pressurizes the support plate 310 while linearly moving along the hole 303 when the driving unit 210 operates. The back of the support plate 310 is seated in a support 304 within the tip module. The front of the support plate 310 is pressurized by an elastic member 330 positioned within the tip module. When the output terminal 211 moves and pressurizes the support plate 310, the support plate 310 is separated from the support 304 and is advanced. Accordingly, the plurality of needles 320 pop out to the front of the through hole 302 and is inserted into a skin tissue. Furthermore, when the output terminal 211 is retracted by the driving of the driving unit 210, the support plate 310 is retracted by the restoring force of the elastic member 330, and thus the plurality of needles 320 also returns to the inside of the tip module. Although not separately shown in the drawing, a separate guide member for guiding the path along which the aforementioned support plate moves may be further provided.

Although not specifically shown in the drawing, the circuit of the support plate 310 may be configured to be electrically connected to the RF generator of the main body when the tip module is positioned in the handpiece. Alternatively, the circuit of the support plate may be selectively configured to be electrically connected to the RF generator when the support plate is pressurized by the output terminal 211 (e.g., an electrode may be formed at the end of the output terminal and may be electrically connected to the support plate upon pressurization).

Figure 21:
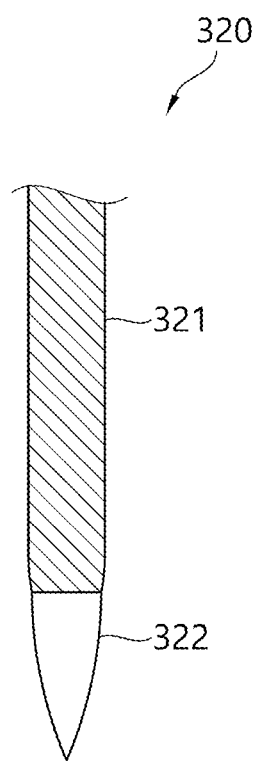
FIG. 21 is a cross-sectional view showing a cross section of one of a plurality of needles of FIG. 20.

FIG. 21 is a cross-sectional view showing a cross section of one of the plurality of needles of FIG. 20. Each needle 320 may be a micro needle having a diameter of approximately 5 to 500 µm. The needle 320 is made of a conductive material so that it can transfer RF energy. A portion that belongs to a surface of each needle and that excludes a tip thereof is made of an insulating material 321 so that RF energy is not transferred to a tissue. Accordingly, part of the tip of each needle functions as an electrode 322, and the needle is configured to transfer RF energy to a tissue through the tip. Accordingly, during treatment, the needle can selectively transfer RF energy to a portion where the end of the needle is positioned.

Referring back to FIG. 20, a bending sensing unit 370 is provided at the end of the handpiece 200. The bending sensing unit 370 includes a plurality of motion sensors disposed along the periphery of the path along which the micro needles proceed. Accordingly, the bending sensing unit 370 may measure whether bending occurs and/or the degree of bending while the micro needles are inserted. The motion sensors include image capturing devices and may sense the bending characteristics of the micro needles while the micro needles are inserted. Alternatively, the motion sensors are configured to sense a change in the location of a marker (e.g., a magnetic body) formed in the length direction of the micro needles, and may sense the bending characteristics of the micro needles by sensing the progress path of the micro needles while the micro needles are inserted. Alternatively, the motion sensor includes a light radiation unit 370a provided on one side of the progress path of the micro needle and an imaging device 370b provided on the other side thereof, and may sense whether the needle is bent or not during insertion using information of light received by the imaging device.

Meanwhile, a displacement sensing unit 360 is provided at the end of the handpiece 200. The displacement sensing unit 360 measures displacement of a skin surface during treatment. For example, the displacement sensing unit 360 includes a movable member 340 movably positioned in the insertion direction of the needles 320 and a sensing member 350 detecting the amount of movement of the movable member.

As shown in FIG. 20, the movable member 340 may be provided in the tip module. Movable member holes 305 are formed at both ends of the tip module, so the movable member 340 is positioned in a form to penetrate the tip module along the movable member holes 305. A stopper 341 having a greater diameter than the movable member hole may be formed in the body of the movable member 340.

Accordingly, the movable member 340 can freely move without restriction in the vertical direction, that is, in the moving direction of the needles, within the range in which the movement of the movable member 340 is not restricted by the stopper 341. At this time, the front part of the movable member 340 coming into contact with a surface of a skin tissue during treatment may be configured to be exposed toward the front of the tip module in a maximum advancement state and to be received within the tip module in a maximum retraction state. Furthermore, the rear part of the movable member 340 may be configured to be protruded toward the back of the tip module in a maximum advancement state and maximum retracted state.

The sensing member 350 is configured to be positioned within the main body 100 of the handpiece separately from the tip module (refer to FIG. 20), and detects the amount of movement of the movable member 340. For example, the sensing member 350 is configured to detect a change in the magnetic field. Furthermore, the sensing member 350 may detect a change in the magnetic field according to a movement of a magnetic body 342 provided at the back of the movable member, and may measure the amount of movement of the movable member 340 based on the detected change.

Figure 22:
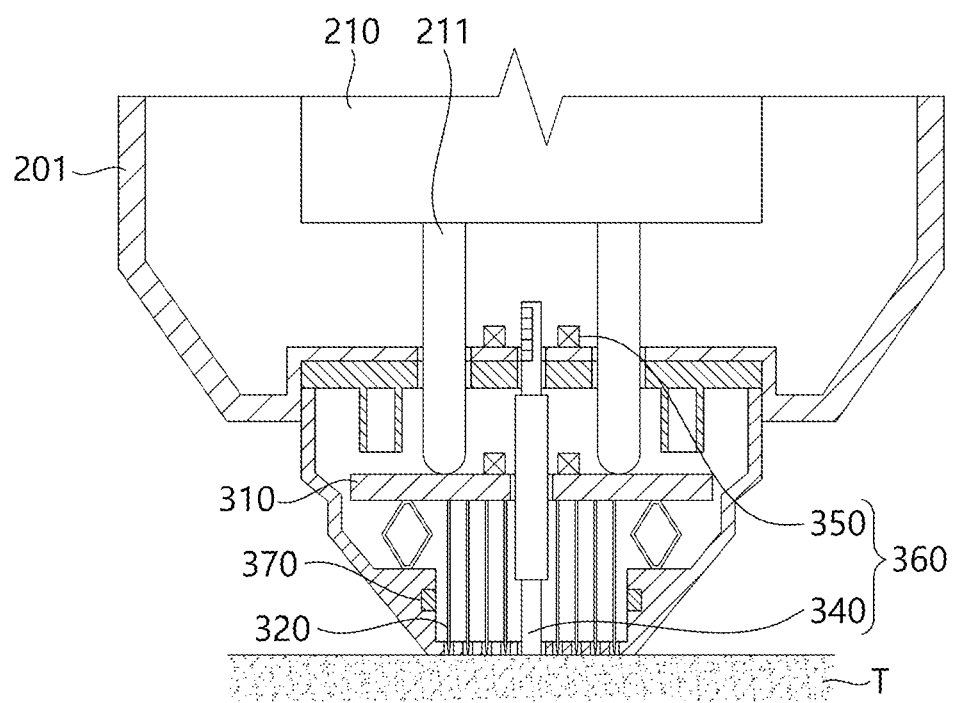
FIG. 22 is a cross-sectional view showing the state right before the needles are inserted during a treatment process using the handpiece of FIG. 20.
Figure 23:
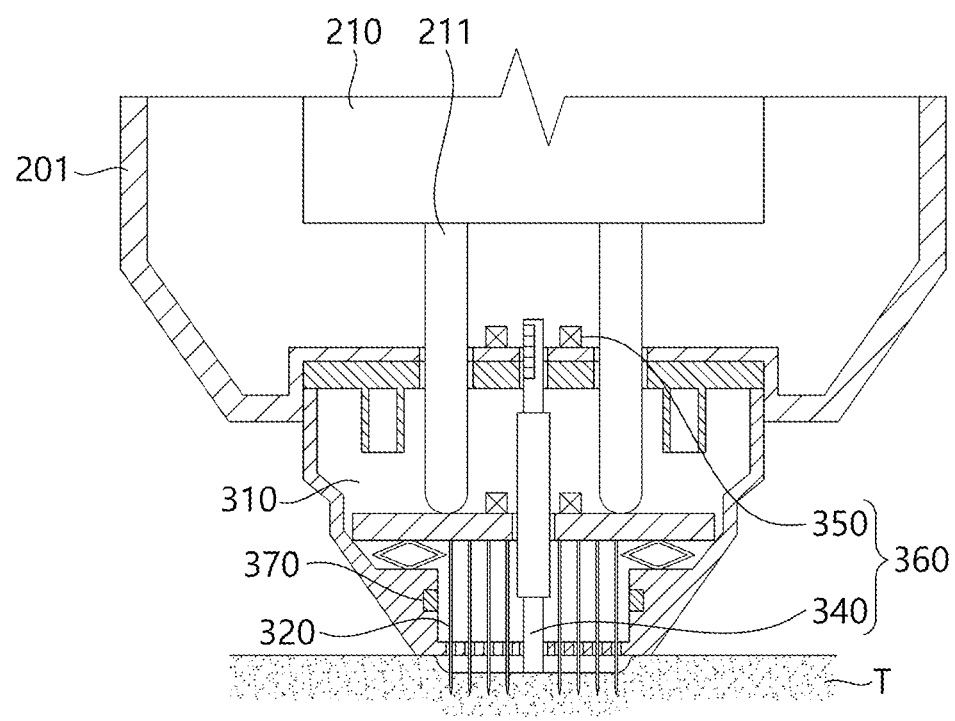
FIG. 23 is a cross-sectional view showing the state in which the needles have been inserted during a treatment process using the handpiece of FIG. 20.

FIG. 22 is a cross-sectional view showing the state right before the needles are inserted during a treatment process using the handpiece of FIG. 20. FIG. 23 is a cross-sectional view showing the state in which the needles have been inserted during a treatment process using the handpiece of FIG. 20.

As shown in FIG. 22, upon treatment, the end (the end equipped with the needles) of the handpiece is downward positioned to come into contact with a skin tissue T. In this case, the movable member 340 moves downward by gravity, comes into contact with the skin surface, and maintains the state in which it is supported by the skin surface. Furthermore, as shown in FIG. 23, when downward displacement occurs in the skin surface due to the insertion of the needles 320, the movable member 340 also moves downward by the displacement of the skin surface. At this time, the sensing member may measure the displacement of the skin surface by measuring the amount of movement of the movable member 340.

Figure 24:
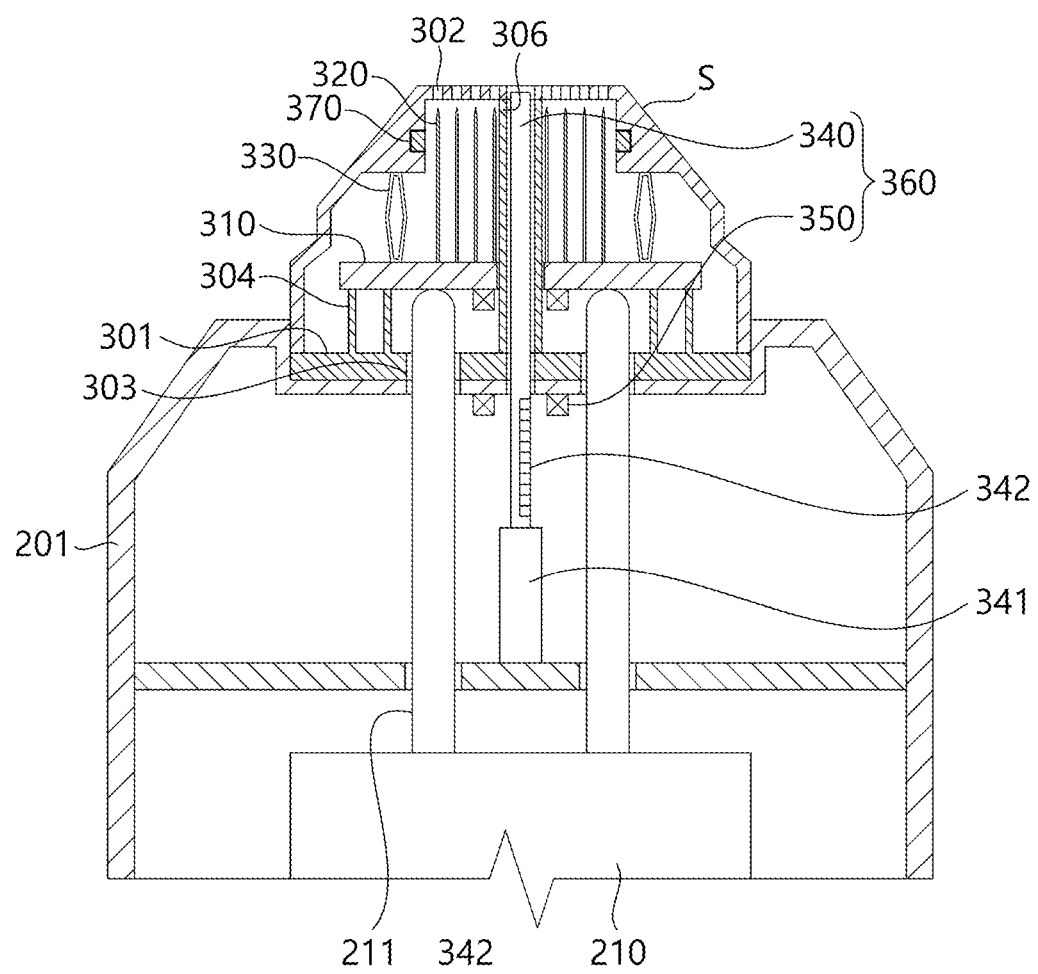
FIG. 24 is a cross-sectional view showing a modified embodiment of the handpiece of FIG. 19.

FIG. 24 is a cross-sectional view showing a modified embodiment of the handpiece of FIG. 19. In FIG. 20, the movable member of the displacement sensing unit has been configured to be included in the tip module and the sensing member has been configured to be included in the main body of the handpiece. In contrast, as shown in FIG. 24, both the movable member and the sensing member may be configured to be included in the main body of the handpiece.

As shown in FIG. 24, a channel 306 through which the movable member can penetrate may be provided at the center of the tip module 300. Furthermore, the movable member 340 is positioned within the main body 201 of the handpiece to freely move in the insertion direction of the needles within the range in which the movable member 340 is not restricted by the stopper 341. At this time, the front part of the movable member 340 may be configured to be protruded and exposed toward the front of the tip module in a maximum advancement state, and may be configured to be received within the channel 306 of the tip module in a maximum retraction state. Furthermore, the sensing member 350 is positioned close to the back of the movable member 340, and may measure the amount of movement of the movable member 340 by sensing a change in the magnetic field by the magnetic body 342 positioned in the movable member.

Figure 25:
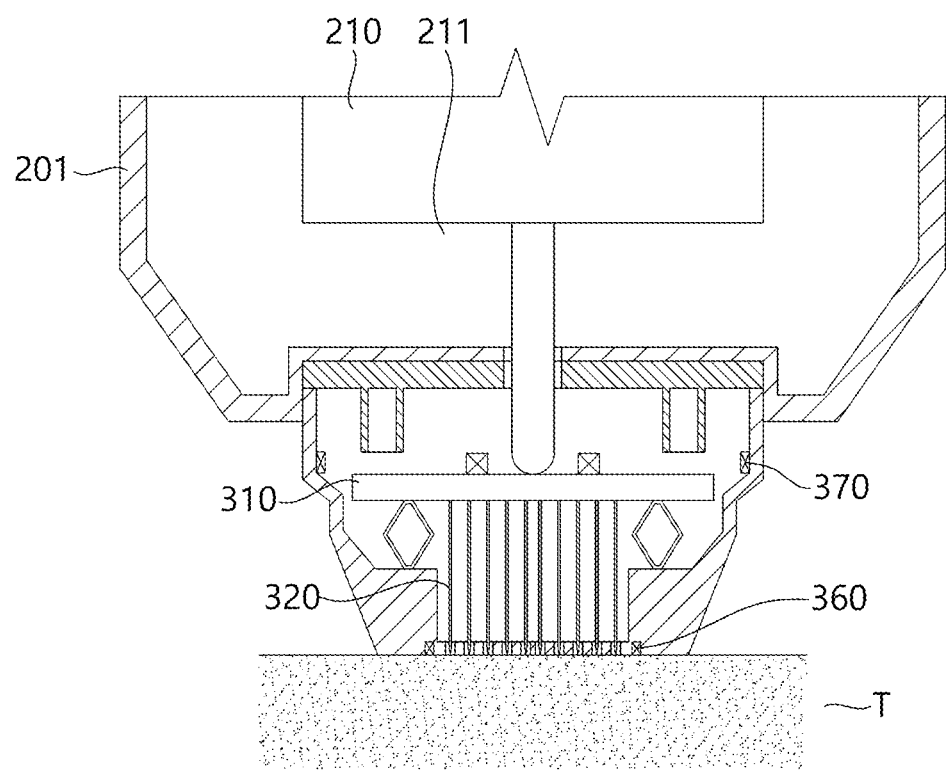
FIG. 25 is a cross-sectional view showing another modified embodiment of the handpiece of FIG. 19.

FIG. 25 is a cross-sectional view showing another modified embodiment of the handpiece of FIG. 19. In FIG. 25, the displacement sensing unit 360 does not include a movable member and a sensing member, but may sense displacement of a tissue using a photosensor positioned at the end of a skin contact surface of the handpiece. Furthermore, as in the method shown in FIGS. 2 to 5, the bending sensing unit 370 includes a plurality of sensors disposed along the periphery of the support plate on the inner wall of the handpiece, and may sense whether bending has occurred by measuring the gradient of the support plate.

Although FIGS. 20 and 25 show the configurations of various displacement sensing units as described above, the displacement sensing unit may be changed and implemented in other forms.

As in the aforementioned embodiments, the treatment apparatus of the present embodiment may perform treatment in such a manner that the operations of the driving unit 210 and the RF generator (an element corresponding to the treatment operation unit of FIG. 6) are controlled and thus the plurality of needles 320 corresponding to the insertion unit (refer to 10 of FIG. 6) is inserted into a skin tissue and transfers RF energy to a target location.

In this case, the controller may control the treatment operation by taking into consideration displacement information of a skin surface occurring due to the insertion of the insertion unit during treatment and information about the occurrence of the bending of the insertion unit when the insertion unit is inserted. If it is determined that bending has not occurred, the controller performs the operation of the first mode as a normal mode. If it is determined that bending has occurred, the controller performs the operation of the second mode for error compensation for the occurrence of the bending. Control contents into which such displacement and bending have been taken into consideration comply with the control step described with reference to FIGS. 12 to 17 of the aforementioned embodiments, and a detailed description of each step is omitted in order to avoid redundancy of the description.

The ends of the micro needles of the treatment apparatus reach an accurate target location through such an operation and transfer RF energy to the target location, thereby being capable of performing treatment. Accordingly, the RF energy is delivered to the dermal layer corresponding to the target location and heats the dermal layer, thereby being capable of causing the contraction of collagen to form a new collagen structure. Furthermore, when the treatment, is completed, the controller may drive the driving unit so that the plurality of needles is drawn out from the tissue, thereby being capable of terminating the treatment.

In this case, the step of setting the first length depending on a shape of the handpiece and an insertion method in the aforementioned step may be differently performed. Hereinafter, symbols are defined as follows for convenience of description.

L1: First length

Ld: Distance from a tissue surface to a target location in the normal state

Ld': Distance from the tissue surface to the target location in the pressurized state L0: Distance that the end of the insertion unit has advanced from the initial location of the insertion unit until it reaches the tissue surface First, as shown in FIGS. 2 to 5, if a tissue surface is not separately pressurized before the tissue surface is pressurized by the insertion unit, a value of the first length L1 may be set as a value of Ld as described above.

In this case, if a contact surface of the handpiece and the end of the insertion unit are separated when the handpiece is positioned, the end of the insertion unit needs to advance by a given distance until it reaches the tissue surface. Accordingly, in this case, a value of the first length L1 may be set as a value of the sum of a value of the Ld and a value of the L0.

Moreover, a tissue surface has already been pressurized before the insertion unit pressurizes the tissue surface. For example, when the handpiece is positioned, the insertion unit may be inserted in the state in which a tissue surface has been pressurized through a contact surface of the handpiece. This state may be different from the state in which the distance from the tissue surface to a target location has not been pressurized depending on a characteristic of the tissue. Accordingly, in this case, a value of the first length L1 may be set as a value of the Ld' or may be set as a value of the sum of a value of the Ld' and a value of the L0. In this case, a value of the Ld' may be obtained using previously stored information of the database depending on the type of tissue.

Figure 26:
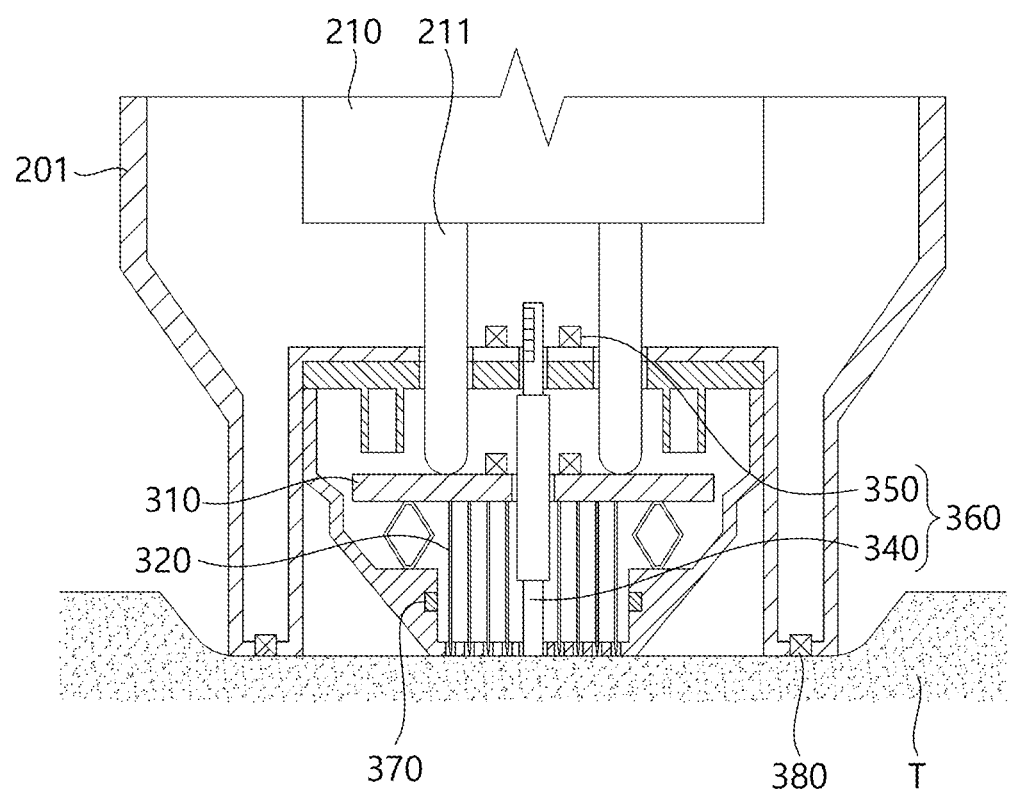
FIG. 26 is a cross-sectional view showing a cross section of the handpiece in an insertion operation according to another embodiment.

FIG. 26 is a cross-sectional view showing a cross section of the handpiece in an insertion operation according to another embodiment. FIG. 26 shows an element further including a pressure sensor 380 at the end of the handpiece compared to the aforementioned embodiment. FIG. 26 shows a structure in which a contact surface is formed at the bottom of the case of the main body of the handpiece and the pressure sensor is positioned on the contact surface, but the end of a tip includes a contact surface and the pressure sensor is positioned at the end of the tip.

The pressure sensor may measure a force that a tissue surface is pressurized by a contact surface before the insertion operation of the insertion unit is performed. In this case, the controller may measure the amount of applied pressure through the pressure sensor and insert the insertion unit by controlling the driving unit when the applied pressure reaches a specific amount so that the insertion operation of the insertion unit is performed in the state in which tension of a given amount or more has been formed in the skin surface.

If the separate pressure sensor is provided in the contact surface as in the present embodiment, a value of the Ld' can be precisely checked in real time. A value of the Ld' can be accurately checked using measured information and information (e.g., the graph of FIG. 6) stored in the database because the applied pressure of a contact force can be measured in real time when treatment is performed. Accordingly, although applied pressure through a contact surface is greatly changed or a change in the distance up to a target location according to the applied pressure is great, treatment can be performed by accurately setting the first length value.

The treatment apparatus that performs treatment by transferring RF energy to a skin tissue has been chiefly described above. This is an example, and may be applied to a treatment apparatus aimed at another tissue not a skin tissue. Furthermore, the treatment apparatus may be applied to various treatment apparatuses, such as a treatment apparatus performing treatment using a method of transferring a treatment substance in addition to a treatment apparatus performing treatment using a method of transferring RF energy. Moreover, the treatment apparatus including the main body and the handpiece has been basically described, but is not limited thereto, and may be applied to a treatment apparatus configured in a single module form of the handpiece.

Although one embodiment of the present invention has been described in detail, the present invention is not limited to the embodiment. It is to be noted that a person having ordinary skill in the art to which the present invention pertains may modify or change the present invention in various manners without departing from the scope of the technical characteristics of the present invention defined in the claims.

The invention claimed is:

1. A treatment apparatus, comprising:
    an insertion unit comprising a plurality of microneedles and configured to be inserted into a tissue located in a dermal layer or a subcutaneous fat layer through a skin surface;
    a state sensing unit sensing a state of the insertion unit during insertion; and
    a controller controlling an insertion operation of the insertion unit based on information sensed by the state sensing unit,
    wherein the state sensing unit comprises a bending sensing unit sensing bending of the insertion unit occurring during insertion, and
    wherein when the bending of the insertion unit is sensed by the bending sensing unit, the controller controls the insertion operation of the insertion unit so that an end of the insertion unit reaches a target location in a state in which the bending of the insertion unit has been restored.

2. The treatment apparatus of claim 1, wherein when the bending of the insertion unit is sensed by the bending sensing unit, the controller advances the insertion unit up to a restoration depth at which the bending is restored and then retracts the end of the insertion unit so that the end of the insertion unit reaches the target location.

3. The treatment apparatus of claim 2, wherein the restoration depth is positioned in a layer having a lower insertion resistance characteristic than a surface layer of the skin.

4. The treatment apparatus of claim 2, wherein the controller waits for a restoration time for which the bending of the insertion unit is restored in the state in which the insertion unit has been advanced up to the restoration depth, and then retracts the insertion unit.

5. The treatment apparatus of claim 4, wherein the waiting time is between 0.05 second to 1 second.

6. The treatment apparatus of claim 4, wherein the waiting time is controlled based on a degree of the bending of the insertion unit sensed by the bending sensing unit.

7. The treatment apparatus of claim 1, wherein the controller controls the insertion operation in a first mode when the bending of the insertion unit sensed by the bending sensing unit is a reference value or less and controls the insertion operation in a second mode when the bending of the insertion unit sensed by the bending sensing unit exceeds the reference value.

8. The treatment apparatus of claim 1, wherein the bending sensing unit senses whether the bending of the insertion unit occurs based on whether a support plate in which the insertion unit is positioned is inclined.

9. The treatment apparatus of claim 1, wherein the bending sensing unit comprises a motion sensor positioned at a location close to an end of the handpiece and sensing whether the insertion unit has been bent.

10. The treatment apparatus of claim 1, further comprising a displacement sensing unit measuring displacement of the skin surface occurring due to the insertion of the insertion unit,
    wherein the controller controls the insertion operation of the insertion unit by taking into consideration displacement sensed by the displacement sensing unit.

11. The treatment apparatus of claim 10, wherein the controller additionally inserts the insertion unit in accordance with displacement occurring in the skin surface.

12. The treatment apparatus of claim 1, wherein the insertion unit comprises a plurality of micro needles.

13. The treatment apparatus of claim 12, wherein the micro needle has a diameter of 10 to 1000 μm.

14. The treatment apparatus of claim 1, wherein the insertion unit comprises an energy transfer member transferring energy to the target location in the state in which the insertion unit has been inserted into the tissue.

15. The treatment apparatus of claim 14, wherein when the bending is sensed to be not restored through the insertion operation, the controller controls to transfer energy having lower output than preset energy to the target location or to not transfer energy to the target location.

16. A treatment apparatus, comprising:
    a handpiece;
    an insertion unit comprising a plurality of microneedles and configured to advance and retract to and from one side of the handpiece and inserted into a tissue located in dermal layer or subcutaneous fat layer to transfer energy to a target location;
    a bending sensing unit sensing bending of the insertion unit occurring during insertion of the insertion unit; and
    a controller controlling an insertion operation of the insertion unit based on information sensed by the bending sensing unit,
    wherein when the bending of the insertion unit is sensed by the bending sensing unit, the controller controls the insertion operation of the insertion unit so that an end of the insertion unit reaches a target location in a state in which the bending of the insertion unit has been restored.

17. A method of controlling a treatment apparatus, comprising steps of:
- positioning an insertion unit comprising a plurality of micro needles on a tissue surface;
- inserting the insertion unit into a tissue located in a dermal layer or a subcutaneous fat layer by advancing the insertion unit;
- sensing bending of the insertion unit occurring during the insertion of the insertion unit; and
- controlling an insertion operation of the insertion unit based on the sensed bending information,
- wherein when the bending of the insertion unit is sensed by a bending sensing unit, the controller controls the insertion operation of the insertion unit so that an end of the insertion unit reaches a target location in a state in which the bending of the insertion unit has been restored.

18. The method of claim 17, wherein the step of controlling the insertion operation comprises:
- advancing the insertion unit up to a restoration depth at which the bending is restored, and
- then retracting the insertion unit to a target location when the bending of the insertion unit is sensed through the bending sensing unit.

19. The method of claim 18, wherein the step of controlling the insertion operation comprises a step of waiting for a restoration time for which the bending of the insertion unit is stored in the state in which the insertion unit has been advanced up to the restoration depth.

20. The method of claim 19, wherein the restoration time is set based on a degree of the bending of the insertion unit or a time until the bending sensing unit senses that the insertion unit has restored from a bending state.

21. The method of claim 17, wherein the step of controlling the insertion operation comprises:
- controlling the insertion operation in a first mode when a degree of the bending of the insertion unit sensed by the bending sensing unit is a reference value or less, and
- controlling the insertion operation in a second mode when a degree of the bending of the insertion unit sensed by the bending sensing unit exceeds the reference value.

22. The method of claim 17, wherein the step of sensing the bending comprises sensing the bending by measuring a gradient of the support plate in which the insertion unit is positioned.

23. The method of claim 17, wherein the step of sensing the bending comprises sensing whether the insertion unit has been bent using a motion sensor positioned at a location close to an end of the handpiece.

24. The method of claim 17, wherein the treatment apparatus further comprises a displacement sensing unit measuring displacement of the tissue surface occurring due to the insertion of the insertion unit,
- wherein the step of controlling the insertion operation comprises controlling the insertion operation of the insertion unit by taking into consideration displacement sensed by the displacement sensing unit.

25. The method of claim 17, further comprises a step of transferring energy to a target location within the tissue through the insertion unit.

* * * * *